(12) United States Patent
Lau et al.

(10) Patent No.: US 7,291,105 B2
(45) Date of Patent: Nov. 6, 2007

(54) SELF-ANCHORING CARDIAC HARNESS

(75) Inventors: Lilip Lau, Los Altos, CA (US); James Hong, Palo Alto, CA (US); Matthew Fishler, Sunnyvale, CA (US); Craig Mar, Fremont, CA (US); Steven Meyer, Oakland, CA (US)

(73) Assignee: Paracor Medical, Inc., Sunnyvale, CA (US)

( * ) Notice: Subject to any disclaimer, the term of this patent is extended or adjusted under 35 U.S.C. 154(b) by 498 days.

(21) Appl. No.: 10/888,806

(22) Filed: Jul. 8, 2004
(Under 37 CFR 1.47)

(65) Prior Publication Data
US 2005/0054892 A1 Mar. 10, 2005

Related U.S. Application Data

(60) Provisional application No. 60/486,062, filed on Jul. 10, 2003.

(51) Int. Cl.
*A61F 13/00* (2006.01)
(52) U.S. Cl. .......................................... 600/37; 600/16
(58) Field of Classification Search ............ 600/16–18, 600/37; 601/148, 151–153; 602/36–37, 602/75–76; 623/3.1, 3.11–3.12, 3.16–3.17, 623/3.26
See application file for complete search history.

(56) References Cited

U.S. PATENT DOCUMENTS

| 2,826,193 | A | 3/1958 | Vineberg |
| 3,464,322 | A | 9/1969 | Pequignot |
| 3,513,836 | A | 5/1970 | Sausse |
| 3,587,567 | A | 6/1971 | Schiff |
| 3,613,672 | A | 10/1971 | Schiff |
| 3,966,401 | A | 6/1976 | Hancock et al. |
| 3,983,863 | A | 10/1976 | Janke et al. |
| 3,988,782 | A | 11/1976 | Dardik et al. |
| 4,011,947 | A | 3/1977 | Sawyer |
| 4,048,990 | A | 9/1977 | Goetz |
| 4,065,816 | A | 1/1978 | Sawyer |

(Continued)

FOREIGN PATENT DOCUMENTS

DE 3831 540 A1 4/1989

(Continued)

OTHER PUBLICATIONS

Wharton, J. Marcus, et al., *Electrophysiological Effects of Monophasic and Biphasic Stimuli in Normal and Infarcted Dogs*, PACE, vol. 13, pp. 1158-1172, Sep. 1990.

(Continued)

*Primary Examiner*—John P. Lacyk
(74) *Attorney, Agent, or Firm*—Fulwider Patton LLP

(57) ABSTRACT

A self-anchoring cardiac harness is configured to fit at least a portion of a patient's heart and includes a tissue engaging element for frictionally engaging an outer surface of a heart. The engaging element produces sufficient friction relative to the outer surface of the heart, so that the harness does not migrate substantially relative to the heart. There is enough force created by the engaging element that there is no need to apply a suture to the heart in order to retain the cardiac harness. Further, the engaging element is adapted to engage the outer surface of the heart without substantially penetrating the outer surface.

26 Claims, 24 Drawing Sheets

U.S. PATENT DOCUMENTS

| | | |
|---|---|---|
| 4,108,161 A | 8/1978 | Samuels et al. |
| 4,192,293 A | 3/1980 | Asrican |
| 4,211,325 A | 7/1980 | Wright |
| 4,261,342 A | 4/1981 | Aranguren Duo |
| 4,306,318 A | 12/1981 | Mano et al. |
| 4,372,293 A | 2/1983 | Vijil-Rosales |
| 4,403,604 A | 9/1983 | Wilkinson et al. |
| 4,428,375 A | 1/1984 | Ellman |
| 4,512,471 A | 4/1985 | Kaster et al. |
| 4,536,893 A | 8/1985 | Parravicini |
| 4,545,783 A | 10/1985 | Vaughan |
| 4,628,937 A | 12/1986 | Hess et al. |
| 4,630,597 A | 12/1986 | Kantrowitz et al. |
| 4,665,906 A | 5/1987 | Jervis |
| 4,690,134 A | 9/1987 | Snyders |
| 4,697,703 A | 10/1987 | Will |
| 4,750,619 A | 6/1988 | Cohen et al. |
| 4,821,723 A | 4/1989 | Baker, Jr. et al. |
| 4,827,932 A | 5/1989 | Ideker et al. |
| 4,834,707 A | 5/1989 | Evans |
| 4,838,288 A | 6/1989 | Wright et al. |
| 4,840,626 A | 6/1989 | Linsky et al. |
| 4,863,016 A | 9/1989 | Fong et al. |
| 4,878,890 A | 11/1989 | Bilweis |
| 4,936,857 A | 6/1990 | Kulik |
| 4,957,477 A | 9/1990 | Lundbäck |
| 4,960,424 A | 10/1990 | Grooters |
| 4,973,300 A | 11/1990 | Wright |
| 4,976,730 A | 12/1990 | Kwan-Gett |
| 5,031,762 A | 7/1991 | Heacox |
| 5,057,117 A | 10/1991 | Atweh |
| 5,067,957 A | 11/1991 | Jervis |
| 5,087,243 A | 2/1992 | Avitall |
| 5,098,369 A | 3/1992 | Heilman et al. |
| 5,106,386 A | 4/1992 | Isner et al. |
| 5,119,804 A | 6/1992 | Anstadt |
| 5,131,905 A | 7/1992 | Grooters |
| 5,150,706 A | 9/1992 | Cox et al. |
| 5,169,381 A | 12/1992 | Snyders |
| 5,186,711 A | 2/1993 | Epstein |
| 5,190,546 A | 3/1993 | Jervis |
| 5,192,314 A | 3/1993 | Daskalakis |
| 5,197,978 A | 3/1993 | Hess |
| 5,256,132 A | 10/1993 | Snyders |
| 5,279,539 A | 1/1994 | Bohan et al. |
| 5,290,217 A | 3/1994 | Campos |
| 5,336,254 A | 8/1994 | Brennen et al. |
| 5,344,442 A | 9/1994 | Deac |
| 5,352,184 A | 10/1994 | Goldberg et al. |
| 5,356,432 A | 10/1994 | Rutkow et al. |
| 5,366,460 A | 11/1994 | Eberbach |
| 5,383,840 A | 1/1995 | Heilman et al. |
| 5,385,156 A | 1/1995 | Oliva |
| 5,385,229 A | 1/1995 | Bittmann et al. |
| 5,385,528 A | 1/1995 | Wilk |
| 5,405,360 A | 4/1995 | Tovey |
| 5,429,584 A | 7/1995 | Chiu |
| 5,433,727 A | 7/1995 | Sideris |
| 5,456,711 A | 10/1995 | Hudson |
| 5,460,962 A | 10/1995 | Kemp |
| 5,500,015 A | 3/1996 | Deac |
| 5,507,779 A | 4/1996 | Altman |
| 5,509,428 A | 4/1996 | Dunlop |
| 5,524,633 A | 6/1996 | Heaven et al. |
| 5,533,958 A | 7/1996 | Wilk |
| 5,534,024 A | 7/1996 | Rogers et al. |
| 5,545,210 A | 8/1996 | Hess et al. |
| 5,558,617 A | 9/1996 | Heilman et al. |
| 5,571,215 A | 11/1996 | Sterman et al. |
| 5,582,616 A | 12/1996 | Bolduc et al. |
| 5,584,803 A | 12/1996 | Stevens et al. |
| 5,593,424 A | 1/1997 | Northrup III |
| 5,593,441 A | 1/1997 | Lichtenstein et al. |
| 5,597,378 A | 1/1997 | Jervis |
| 5,603,337 A | 2/1997 | Jarvik |
| 5,607,477 A | 3/1997 | Schindler et al. |
| 5,647,372 A | 7/1997 | Tovey et al. |
| 5,647,380 A | 7/1997 | Campbell et al. |
| 5,695,525 A | 12/1997 | Mulhauser et al. |
| 5,702,343 A | 12/1997 | Alferness |
| 5,713,954 A | 2/1998 | Rosenberg et al. |
| 5,727,569 A | 3/1998 | Benetti et al. |
| 5,749,839 A | 5/1998 | Kovacs |
| 5,782,746 A | 7/1998 | Wright |
| 5,799,661 A * | 9/1998 | Boyd et al. .................. 128/898 |
| 5,800,334 A | 9/1998 | Wilk |
| 5,800,528 A | 9/1998 | Lederman et al. |
| 5,814,097 A | 9/1998 | Sterman et al. |
| 5,824,028 A | 10/1998 | Knisley |
| 5,836,311 A | 11/1998 | Borst et al. |
| 5,848,962 A | 12/1998 | Feindt et al. |
| 5,849,005 A | 12/1998 | Garrison et al. |
| 5,853,422 A | 12/1998 | Huebsch et al. |
| 5,865,791 A | 2/1999 | Whayne et al. |
| 5,904,690 A | 5/1999 | Middleman et al. |
| 5,910,124 A | 6/1999 | Rubin |
| 5,927,284 A | 7/1999 | Borst et al. |
| 5,948,019 A | 9/1999 | Shu et al. |
| 5,957,977 A | 9/1999 | Melvin |
| 5,961,440 A | 10/1999 | Schweich, Jr. et al. |
| 5,976,069 A | 11/1999 | Navia et al. |
| 5,979,456 A | 11/1999 | Magovern |
| 5,984,857 A | 11/1999 | Buck et al. |
| 5,990,378 A | 11/1999 | Ellis |
| 6,007,486 A | 12/1999 | Hunt et al. |
| 6,015,378 A | 1/2000 | Borst et al. |
| 6,024,096 A | 2/2000 | Buckberg |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,076,013 A | 6/2000 | Brennan et al. |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,095,968 A | 8/2000 | Snyders |
| 6,110,100 A | 8/2000 | Talpade |
| 6,117,159 A | 9/2000 | Huebsch et al. |
| 6,117,979 A | 9/2000 | Hendriks et al. |
| 6,123,662 A | 9/2000 | Alferness et al. |
| 6,125,852 A | 10/2000 | Stevens et al. |
| 6,126,590 A | 10/2000 | Alferness |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,166,184 A | 12/2000 | Hendriks et al. |
| 6,169,922 B1 | 1/2001 | Alferness et al. |
| 6,174,279 B1 | 1/2001 | Girard |
| 6,179,791 B1 | 1/2001 | Krueger |
| 6,183,411 B1 | 2/2001 | Mortier et al. |
| 6,190,408 B1 | 2/2001 | Melvin |
| 6,193,648 B1 | 2/2001 | Krueger |
| 6,206,820 B1 | 3/2001 | Kazi et al. |
| 6,214,047 B1 | 4/2001 | Melvin |
| 6,217,894 B1 | 4/2001 | Sawhney et al. |
| 6,221,103 B1 | 4/2001 | Melvin |
| 6,224,540 B1 | 5/2001 | Ledermann et al. |
| 6,230,714 B1 | 5/2001 | Alferness et al. |
| 6,258,023 B1 * | 7/2001 | Rogers et al. ................ 600/37 |

| | | |
|---|---|---|
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,282,445 B1 | 8/2001 | Reinhardt et al. |
| 6,287,250 B1 | 9/2001 | Peng et al. |
| 6,293,906 B1 | 9/2001 | Vanden Hoek et al. |
| 6,306,141 B1 | 10/2001 | Jervis |
| 6,312,725 B1 | 11/2001 | Wallace et al. |
| 6,346,077 B1 * | 2/2002 | Taylor et al. ............... 600/204 |
| 6,352,710 B2 | 3/2002 | Sawhney et al. |
| 6,360,749 B1 | 3/2002 | Jayaraman |
| 6,375,608 B1 | 4/2002 | Alferness |
| 6,390,976 B1 | 5/2002 | Spence et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| 6,409,760 B1 | 6/2002 | Melvin |
| 6,416,459 B1 | 7/2002 | Haindl |
| 6,425,856 B1 | 7/2002 | Shapland et al. |
| 6,432,039 B1 | 8/2002 | Wardle |
| 6,451,025 B1 | 9/2002 | Jervis |
| 6,482,146 B1 | 11/2002 | Alferness et al. |
| 6,537,203 B1 | 3/2003 | Alferness et al. |
| 6,544,168 B2 | 4/2003 | Alferness |
| 6,547,821 B1 | 4/2003 | Taylor et al. |
| 6,564,094 B2 | 5/2003 | Alferness et al. |
| 6,567,699 B2 | 5/2003 | Alferness et al. |
| 6,569,082 B1 | 5/2003 | Chin |
| 6,572,533 B1 | 6/2003 | Shapland et al. |
| 6,575,921 B2 | 6/2003 | Vanden Hoek et al. |
| 6,582,355 B2 | 6/2003 | Alferness et al. |
| 6,587,734 B2 | 7/2003 | Okuzumi |
| 6,595,912 B2 | 7/2003 | Lau et al. |
| 6,602,184 B2 | 8/2003 | Lau et al. |
| 6,612,978 B2 | 9/2003 | Lau et al. |
| 6,612,979 B2 | 9/2003 | Lau et al. |
| 6,633,780 B1 | 10/2003 | Berger |
| 6,645,139 B2 | 11/2003 | Haindl |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,689,048 B2 | 2/2004 | Vanden Hoek et al. |
| 6,695,769 B2 | 2/2004 | French et al. |
| 6,699,259 B2 | 3/2004 | Fogarty et al. |
| 6,701,929 B2 | 3/2004 | Hussein |
| 6,702,732 B1 | 3/2004 | Lau et al. |
| 6,723,041 B2 | 4/2004 | Lau et al. |
| 6,730,016 B1 | 5/2004 | Cox et al. |
| 6,755,779 B2 | 6/2004 | Vanden Hoek et al. |
| 6,759,431 B2 | 7/2004 | Hunter et al. |
| 6,818,018 B1 | 11/2004 | Sawhney |
| 6,833,408 B2 | 12/2004 | Sehl et al. |
| 6,846,296 B1 * | 1/2005 | Milbocker et al. .......... 601/153 |
| 6,876,887 B2 | 4/2005 | Okuzumi |
| 7,022,063 B2 | 4/2006 | Lau et al. |
| 7,155,295 B2 | 12/2006 | Lau et al. |
| 7,189,203 B2 | 3/2007 | Lau et al. |
| 2001/0029314 A1 | 10/2001 | Alferness et al. |
| 2001/0047122 A1 | 11/2001 | Vanden Hoek et al. |
| 2002/0007216 A1 | 1/2002 | Melvin |
| 2002/0019580 A1 | 2/2002 | Lau et al. |
| 2002/0022880 A1 | 2/2002 | Melvin |
| 2002/0068849 A1 | 6/2002 | Schweich, Jr. et al. |
| 2002/0077524 A1 | 6/2002 | Schweich, Jr. et al. |
| 2002/0082647 A1 | 6/2002 | Alferness et al. |
| 2002/0091296 A1 | 7/2002 | Alferness |
| 2002/0103511 A1 | 8/2002 | Alferness et al. |
| 2002/0151950 A1 | 10/2002 | Okuzumi |
| 2003/0060674 A1 | 3/2003 | Gifford, III et al. |
| 2003/0060677 A1 | 3/2003 | French et al. |
| 2003/0060895 A1 | 3/2003 | French et al. |
| 2003/0065248 A1 | 4/2003 | Lau et al. |
| 2003/0199733 A1 | 10/2003 | Shapland et al. |
| 2003/0199955 A1 | 10/2003 | Struble et al. |
| 2003/0229265 A1 | 12/2003 | Girard et al. |
| 2004/0064014 A1 * | 4/2004 | Melvin et al. ............... 600/37 |
| 2004/0133069 A1 | 7/2004 | Shapland et al. |
| 2004/0171907 A1 | 9/2004 | Alferness et al. |
| 2004/0171908 A1 | 9/2004 | Alferness et al. |
| 2004/0267086 A1 * | 12/2004 | Anstadt et al. ............... 600/17 |

FOREIGN PATENT DOCUMENTS

| | | |
|---|---|---|
| DE | 38 31 540 C2 | 6/1993 |
| DE | 295 17 393 U1 | 3/1996 |
| EP | 0 370 931 A1 | 5/1990 |
| EP | 0 280 564 B1 | 6/1993 |
| EP | 0 583 012 B1 | 7/1996 |
| EP | 0 791 330 A3 | 8/1997 |
| EP | 0 919 193 A1 | 6/1999 |
| FR | 2 527 435 | 12/1983 |
| FR | 2 645 739 | 10/1990 |
| GB | 2 115 287 A | 9/1983 |
| GB | 2 209 678 A | 5/1989 |
| JP | 60-203250 | 10/1985 |
| JP | 1-145066 | 6/1989 |
| JP | 1-271829 | 10/1989 |
| SU | 3316206/28-13 | 4/1983 |
| SU | 1734767 A1 | 5/1992 |
| WO | WO 91/19465 | 12/1991 |
| WO | WO 95/06447 | 3/1995 |
| WO | WO 96/04852 | 2/1996 |
| WO | WO 96/40356 | 12/1996 |
| WO | WO 97/20505 | 6/1997 |
| WO | WO 97/24101 | 7/1997 |
| WO | WO 98/03213 | 1/1998 |
| WO | WO 98/14136 | 4/1998 |
| WO | WO 98/26738 | 6/1998 |
| WO | WO 98/29041 | 7/1998 |
| WO | WO 98/58598 | 12/1998 |
| WO | WO 99/11201 | 3/1999 |
| WO | WO 99/30647 | 6/1999 |
| WO | WO 99/44534 | 9/1999 |
| WO | WO 99/44680 | 9/1999 |
| WO | WO 99/53977 | 10/1999 |
| WO | WO 99/56655 | 11/1999 |
| WO | WO 00/02500 | 1/2000 |
| WO | WO 00/06026 | 2/2000 |
| WO | WO 00/06027 | 2/2000 |
| WO | WO 00/06028 | 2/2000 |
| WO | WO 00/13722 | 3/2000 |
| WO | WO 00/16700 | 3/2000 |
| WO | WO 00/18320 | 4/2000 |
| WO | WO 00/28912 | 5/2000 |
| WO | WO 00/28918 | 5/2000 |
| WO | WO 00/43919 | 7/2000 |
| WO | WO 00/45735 | 8/2000 |
| WO | WO 00/48795 | 8/2000 |
| WO | WO 00/62727 | 10/2000 |
| WO | WO 00/74769 | 12/2000 |
| WO | WO 01/17437 | 3/2001 |
| WO | WO 01/21098 | 3/2001 |
| WO | WO 01/50981 | 7/2001 |
| WO | WO 01/67985 | 9/2001 |
| WO | WO 01/85061 | 11/2001 |
| WO | WO 01/91667 | 12/2001 |
| WO | WO 01/95830 | 12/2001 |
| WO | WO 01/95831 | 12/2001 |
| WO | WO 01/95832 | 12/2001 |
| WO | WO 02/13726 | 2/2002 |
| WO | WO 02/19917 | 3/2002 |
| WO | WO 03/026483 | 4/2003 |

| WO | WO 03/026484 | 4/2003 |
| WO | WO 03/026485 | 4/2003 |

OTHER PUBLICATIONS

Shabetai, Ralph, *The Role of the Pericardium in the Pathophysiology of Heart Failure*, Congestive Heart Failure, Second Edition, Chapter 9, pp. 157-187, 2000.

Cohn, Jay N., M.D., *The Management of Chronic Heart Failure*, The New England Journal of Medicine, vol. 335, No. 7, pp. 490-498, Aug. 15, 1996.

Bencini, Adriano, M.D., *The "Pneumomassage" of the Heart*, Surgery, vol. 39, No. 3, Mar. 1956.

Anstadt, George L., et al., *A New Instrument for Prolonged Mechanical Cardiac Massage*, Abstracts of the 38th Scientific Sessions, Supplement II to Circulation, vols. 31 and 32, pp. 375-384, Oct. 1965.

Lev, Maurice, M.D., et al., *Single (Primitive) Ventricle*, Circulation, vol. 39, pp. 577-591.

Paling, D.F., *Warp Knitting Technology*, 1970.

Edie, Richard N., M.D., et al., *Surgical Repair of Single Ventricle*, The Journal of Thoracic and Cardiovascular Surgery, vol. 66, No. 3, pp. 350-360, Sep. 1972.

McGoon, Dwight C., M.D., et al., *Correction of the Univentricular Heart Having Two Atriovantricular Valves*, The Journal of Thoracic and Cardiovascular Surgery, vol. 74, No. 2, pp. 218-226, Aug. 1977.

Doty, Donald B., et al., *Septation of the Univentricular Heart: Transatrial Approach*, The Journal of Thoracic and Cardiovascular Surgery, vol. 78, No. 3, pp. 424-430, Sep. 1979.

Melton, K.N., et al., *Alloys With Two-Shape Memory Effect*, Mechanical Engineering, pp. 42-43, Mar. 1980.

Feldt, Robert H., M.D., et al., *Current Status of the Septation Procedure for Univentricular Heart*, The Journal of Thoracic and Cardiovascular Surgery, vol. 82, No. 1, pp. 93-97, Jul. 1981.

Carpentier, A., et al., *Myocardial Substitution With Stimulated Skeletal Muscle: First Successful Clinical Case*. The Lancet, Jun. 1, 1985.

Anstadt, George L. et al., *Direct Mechanical Ventricular Actuation: A Review*, Resuscitation, pp. 7-23, 1991.

Anstadt, Mark P., M.D., et al., *Pulsatile Reperfusion After Cardiac Arrest Improves Neurologic Outcome*, American Surgery, vol. 214, No. 4, pp. 478-490, Oct. 1991.

Schumacker, Harris B., Jr., *Chapter 21: Cardiac Aneurysms*, The Evolution of Cardiac Surgery, pp. 159-165, 1992.

Savage, Edward B., M.D., et al., *Repair of Left Ventricular Aneurysm*, The Journal of Thoracic and Cardiovascular Surgery, vol. 104, No. 3, pp. 752-762, Sep. 1992.

Carpentier, Alain, M.D., Ph.D., et al., *Dynamic Cardiomyoplasty at Seven Years*, The Journal of Thoracic and Cardiovascular Surgery, vol. 106, No. 1, pp. 42-54, Jul. 1993.

Capouya, Eli R., M.D., et al., *Girdling Effect of Nonstimulated Cardiomyoplasty on Left Ventricular Function*, Annals of Thoracic Surgeons, vol. 56, pp. 867-871, 1993.

Chekanov, Valeri, M.D., Ph.D., *Nonstimulated Cardiomyoplasty Wrap Attenuated the Degree of Left Ventricular Enlargement*, Annals of Thoracic Surgeons, vol. 57, pp. 1684-1690, 1997.

Chiu, Ray C.-J, *Using Skeletal Muscle for Cardiac Assistance*, Scientific American, pp. 68-77, Nov./Dec. 1994.

Kass, David A., M.D., et al., *Reverse Remodeling From Cardiomyoplasty in Human Heart Failure: External Constraint Versus Active Assist*, Circulation, vol. 91, No. 9, pp. 2314-2318, May 1, 1995.

Vaynblat, Mikhail, M.D., et al., *Cardiac Binding in Experimental Heart Failure*, Annals of Thoracic Surgery (Abstract), Supplement to Circulation, vol. 92, Suppl. 1, 1995.

Levin, Howard R., M.D., et al., *Reversal of Chronic Ventricular Dilation in Patients With End-Stage Cardiomyopathy by Prolonged Mechanical Unloading*, Circulation, vol. 91, No. 11, pp. 2717-2720, 1995.

Chaudhry, Pervaiz A., M.D., et al., *Acute Ventricular Reduction with Acorn's Cardiac Support Device Prevents Progressive Left Ventricular Dysfunction and Remodeling in Dogs With Advanced Heart Failure*, Cardiothoracic Surgery, pp. 146-148, 1996.

Oh, Joong Hwan, M.D., et al., *Mechanisms of Dynamic Cardiomyoplasty: Current Concepts*, Journal of Cardiac Surgery, vol. 11, pp. 194-199, 1996.

Badhwar, Vinay, *Power Generation From Four Skeletal Muscle Configurations Design Implications for a Muscle Powered Cardiac Assist Device*, ASAIO Journal, vol. 43, pp. M651-M657, 1997.

Westaby, Stephen, et al., *Landmarks in Cardiac Surgery*, pp. 198-199, 1997.

Cox, James L., *Left Ventricular Aneurysms: Pathophysiologic Observations and Standard Resection*, Seminars in Thoracic and Cardiovascular Surgery, vol. 9, No. 2, pp. 113-122, Apr. 1997.

Coletta, C., et al., *Prognostic Value of Left Ventricular Volume Response During Dobutamine Stress Echocardiography*, European Heart Journal, vol. 18, pp. 1599-1603, Oct. 1997.

Capomolla, Soccorso, M.D., et al., *Dobutamine and Nitroprusside Infusion in Patients With Severe Congestive Heart Failure: Hemodynamic Improvement by Discordant Effects on Mitral Regurgitation, Left Atrial Function, and Ventricular Function*, American Heart Journal, 1089-1098, Dec. 1997.

Oh, Joong Hwan, *The Effects of Prosthetic Cardiac Binding and Adynamic Cardiomyoplasty in a Model of Dilated Cardiomyopathy*, The Journal of Thoracic and Cardiovascular Surgery, vol. 116, No. 1, pp. 148-153, 1998.

Cohn, Jay N., M.D., *Preventing Congestive Heart Failure*, American Family Physician, 6 pages, Apr. 15, 1998.

Cohn, Jay N., M.D., *Structural Basis for Heart Failure: Ventricular Remodeling and Its Pharmacological Inhibition*, Circulation, vol. 91, No. 10, pp. 2504-2507, May 15, 1995.

Gaudron, Peter, M.D., et al., *Progressive Left Ventricular Dysfunction and Remodeling After Myocardial Infarction*, Circulation, vol. 87, pp. 755-763, Mar. 1993.

Pfeiffer, Marc A., M.D., et al., *Ventricular Remodeling After Myocardial Infarction: Experimental Observations and Clinical Implications*, Circulation, vol. 81, No. 4, pp. 1161-1172, Apr. 1990.

Guasp, Francisco Torrent, *Una protesis contentiva para el tratamiento de le microcardiopatia dilatads*, Revista Española de Cardiologia, vol. 51, No. 7, Jul. 1998.

Power, J.M., et al., *Passive Ventricular Constraint Amends the Course of Heart Failure: A Study in an Ovine Model of Dilated Cardiomyopathy*, Cardiovascular Research, vol. 44, pp. 549-555, 1999.

Frazier, O.H., M.D., et al., *Left Ventricular Assist System as a Bridge to Myocardial Recovery*, Annals of Thoracic Surgery, vol. 68, pp. 734-741, 1999.

Melvin, David B., *Ventricular Radium Reduction Without Resection: A Computational Analysis*, ASAIO Journal, pp. 160-165, 1999.

*ABSTRACTS—Heart Failure*, JACC Feb. 1999.

Raman, Jai S., Fracs, et al., *Ventricular Containment as an Adjunctive Procedure in Ischemic Cardiomyopathy: Early Results*, Annals of Thoracic Surgery, vol. 70, pp. 1124-1126, Jan. 2000.

McCarthy, Patrick M., et al., *Device Based Left Ventricular Shape Change Immediately Reduces Left Ventricular Volume and Increases Ejection Fraction in a Pacing Induced Cardiomyopathy Model in Dogs*, JACC, Feb. 2000.

Chaudhry, Pervaiz A., M.D., et al., *Passive Epicardial Containment Prevents Ventricular Remodeling in Heart Failure*, Annals of Thoracic Surgeons, vol. 70, pp. 1275-1280, 2000.

Acorn Cardiovascular, Inc., *CSD Specifications Acorn Cardiac Support Device*, 2000.

*Heart "jacket" could help stop heart failure progression*, Clinicia, No. 916, Jul. 2000.

Acorn Cardiovascular, Inc., *CorCap™ Cardiac Support Device Pamphlet*, Jun. 2001.

*Medtronic's InSync Cardiac Resynchronization Therapy Device Approved by FDA*, (Press Release) Aug. 28, 2001.

Oz, Mehmet C., M.D., *Passive Ventricular Constraint for the Treatment of Congestive Heart Failure*, Annals of Thoracic Surgery, vol. 71, pp. 5185-5187, 2001.

Abstract Supplement, *European Heart Journal*, vol. 22, Sep. 2001.

Gorman, J., *Self-Sutures: New Material Knots Up On Its Own*, Science News, vol. 161, p. 262, Apr. 27, 2002.

Teckell-Taylor, Leah A., et al., *Passive Ventricular Restraint With Nitinol Mesh Attenuates Remodeling Following Acute Myocardial Infarction*, Abstract, American College of Cardiology (Undated).

Mann, Douglas L., M.D., *Basic Mechanisms of Remodeling and Reverse Remodeling*, presented at 6th Annual Scientific Meeting of the Heart Failure Society of America, Sep. 24, 2002.

Bocchi, Edimar a., M.D., *Arrhythmias and Sudden Death After Dynamic Cardiomyoplasty*, Circulation, vol. 90, No. 5, Part 2, pp. 11-107 thru 11-111, Nov. 1994.

Chachques, Juan C., M.D., *Study of Muscular and Ventricular Function in Dynamic Cardiomyoplasty: A Ten-Year Follow-Up*, The Journal of Heart and Lung Transplantation, vol. 16, No. 8, pp. 854-868, Aug. 1997.

Dullum, Mercedes K.C., M.D., et al., *Less Invasive Surgical Management of Heart Failure by Cardiac Support Device Implantation on the Beating Heart*, The Heart Surgery Forum, #2001-1818, pp. 361-363, Jan. 4-7, 2001.

Macris, Michael P. M.D., et al., *Minimally Invasive Access of the Normal Preicardium: Initial Clinical Experience with a Novel Device*, Clinical Cardiology, vol. 22 (Suppl. 1), pp. 1-36 thru 1-39, 1999.

Thakur, Ranjan K., M.D., et al., *Latissimus dorsi Dynamic Cardiomyoplasty: Role of Combined ICD Implantation*, Journal of Cardiac Surgery, vol. 10, pp. 295-297, 1995.

Wharton, J. Marcus, et al., *Electrophysiological Effects of Monophasic and Biphasic Stimuli in Normal and Infarcted Dogs*, PACE, vol. 13, pp. 1158-1172, Sep. 1990.

\* cited by examiner

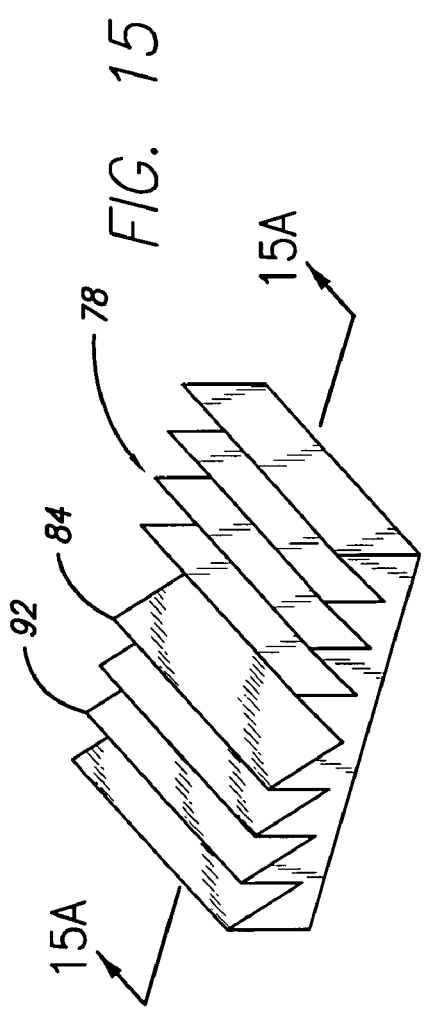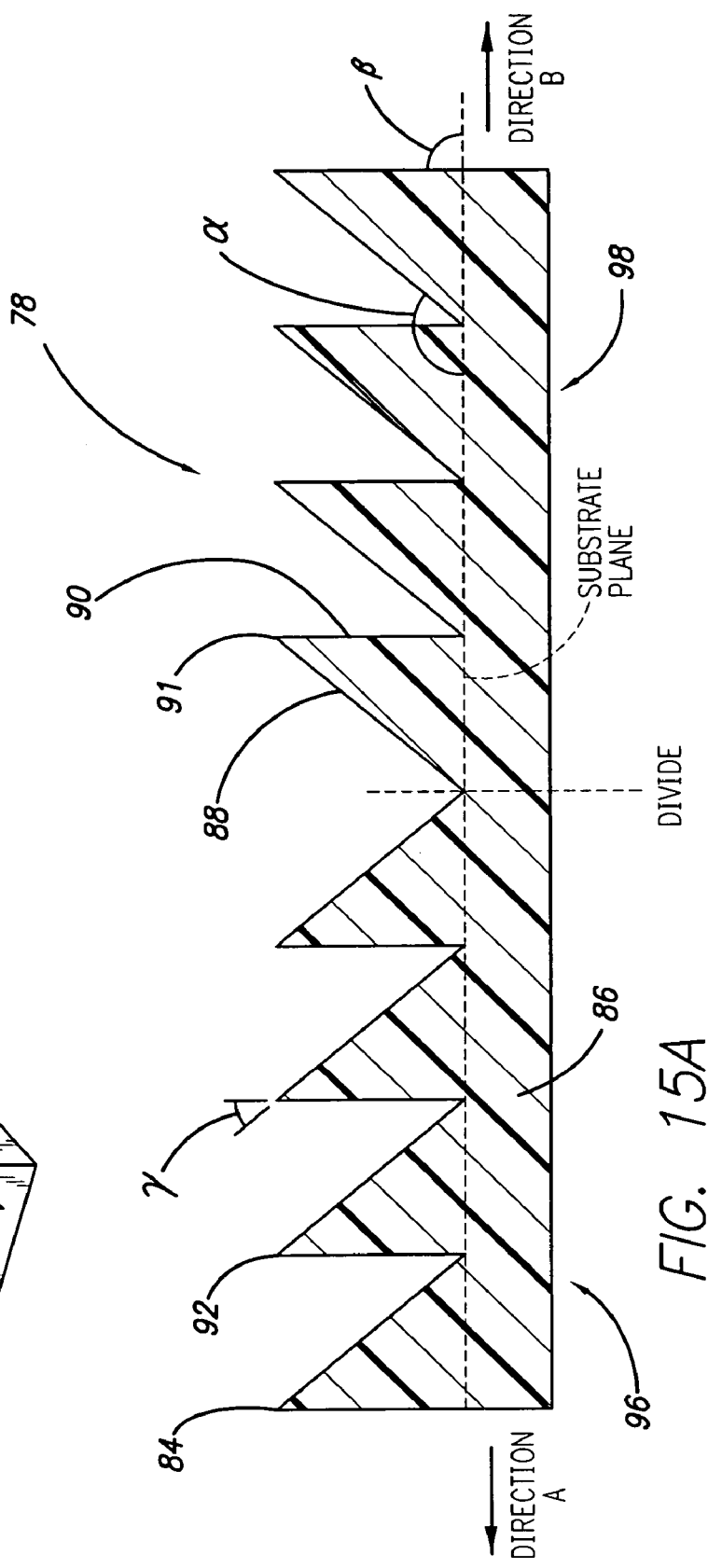
FIG. 15
FIG. 15A

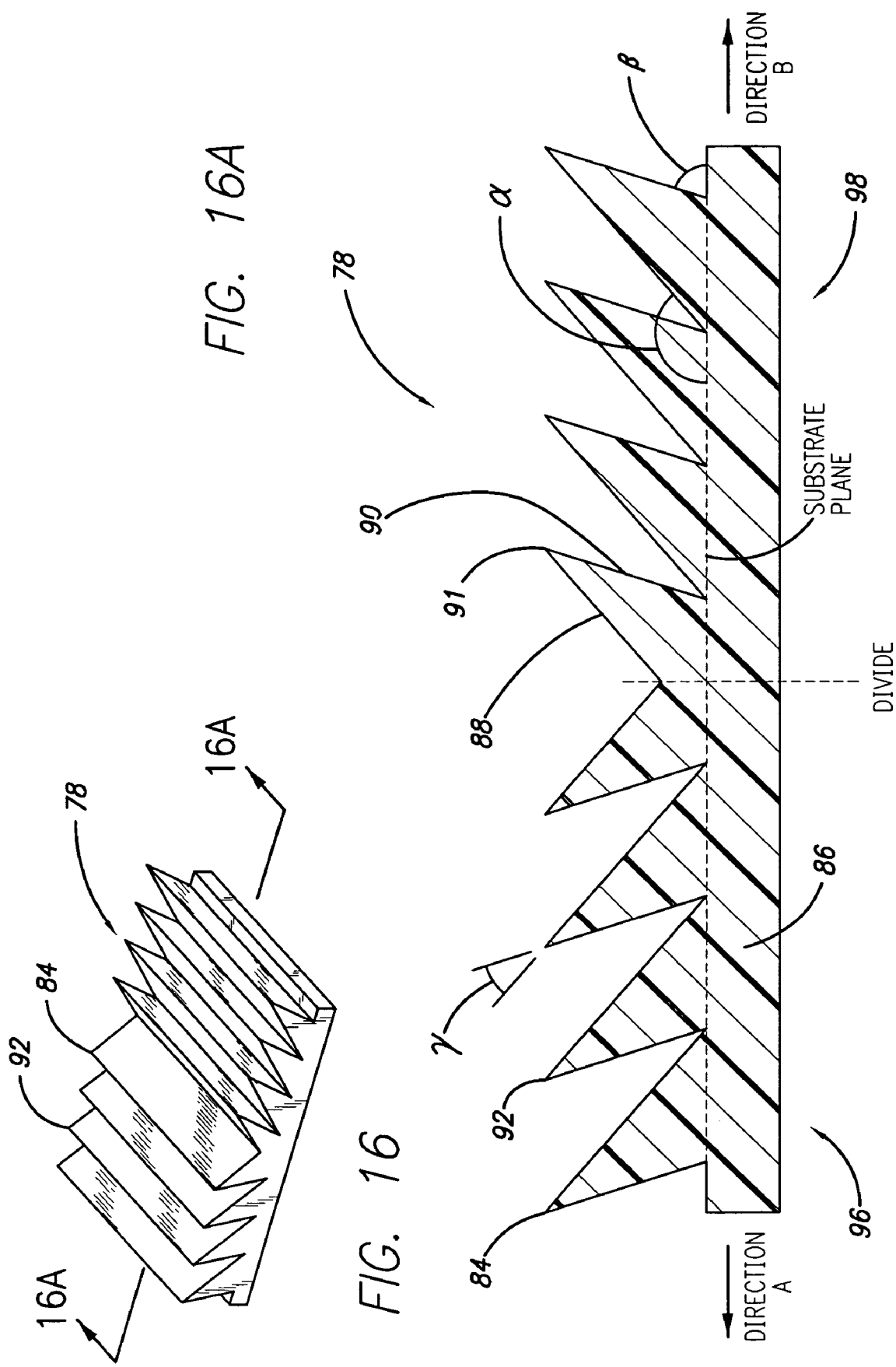

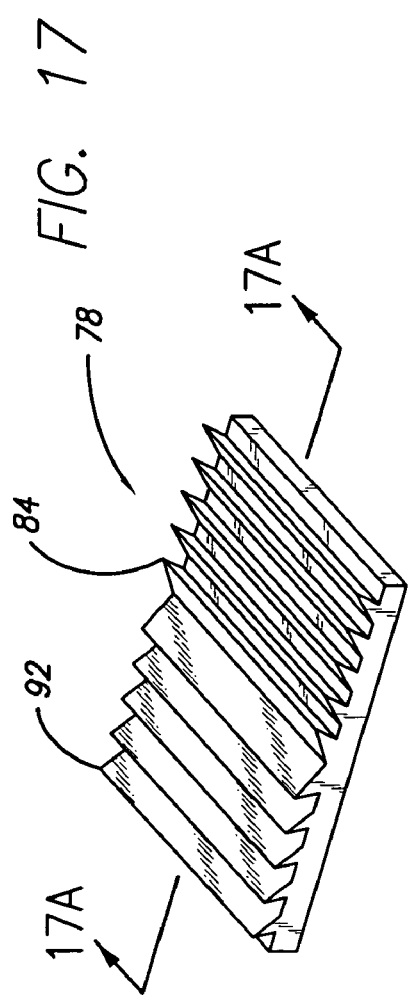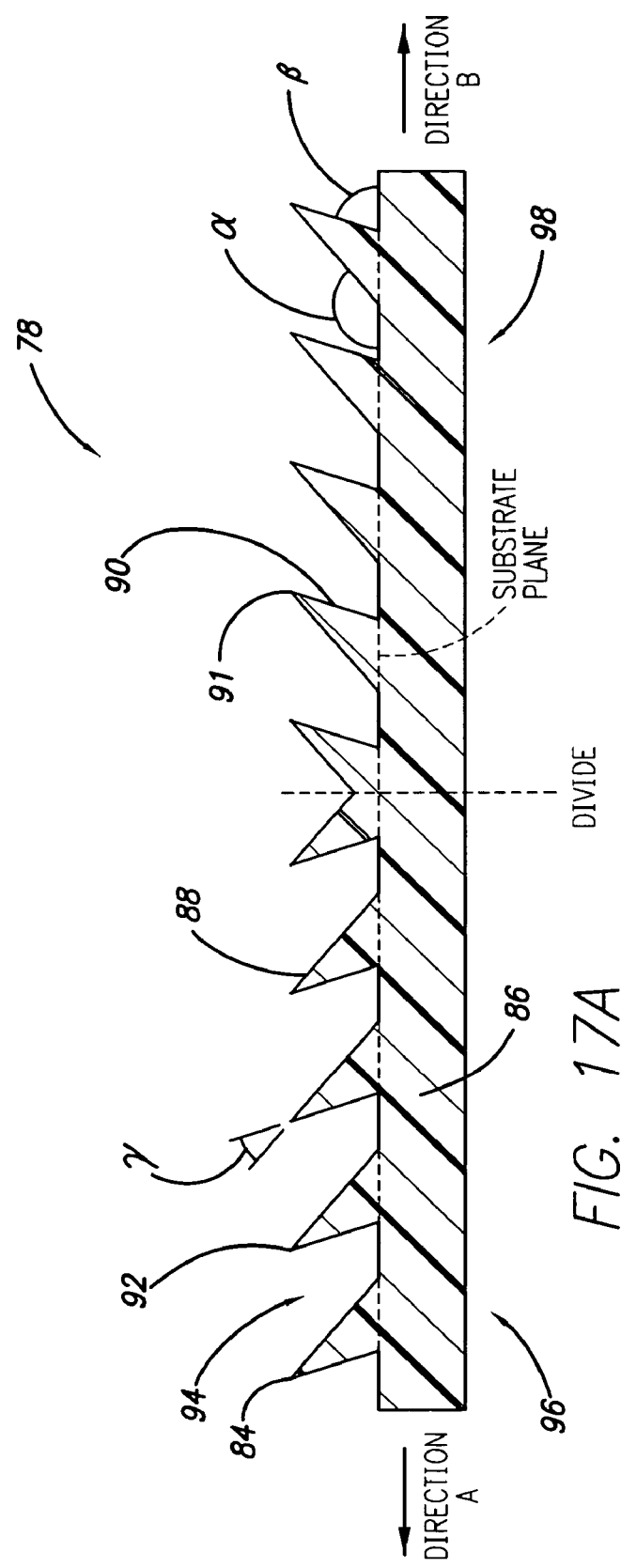

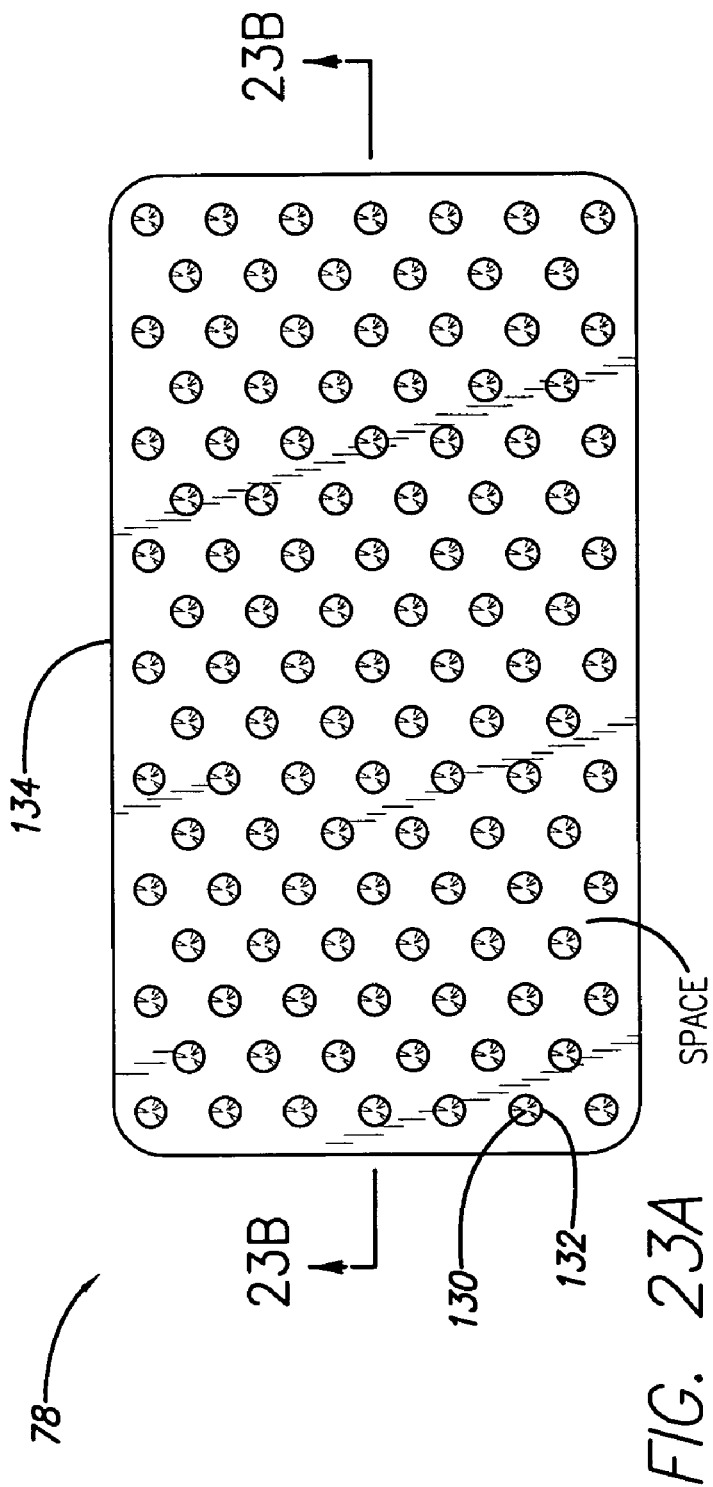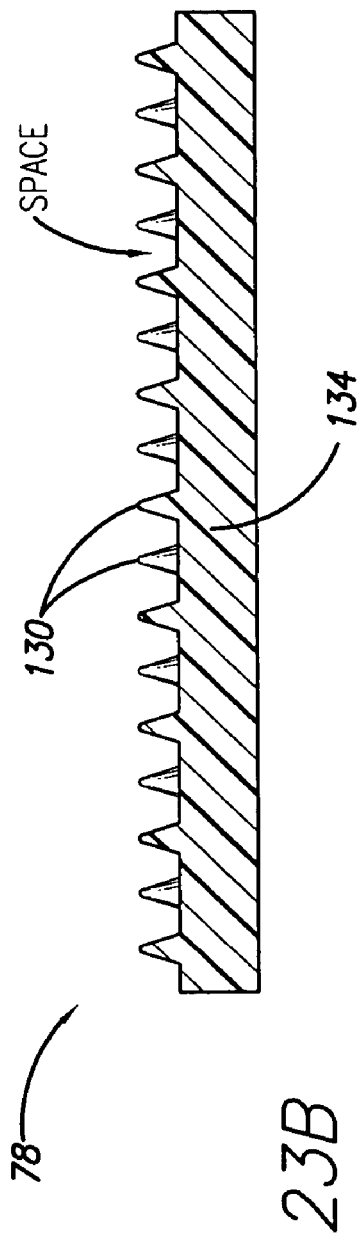
FIG. 23A
FIG. 23B

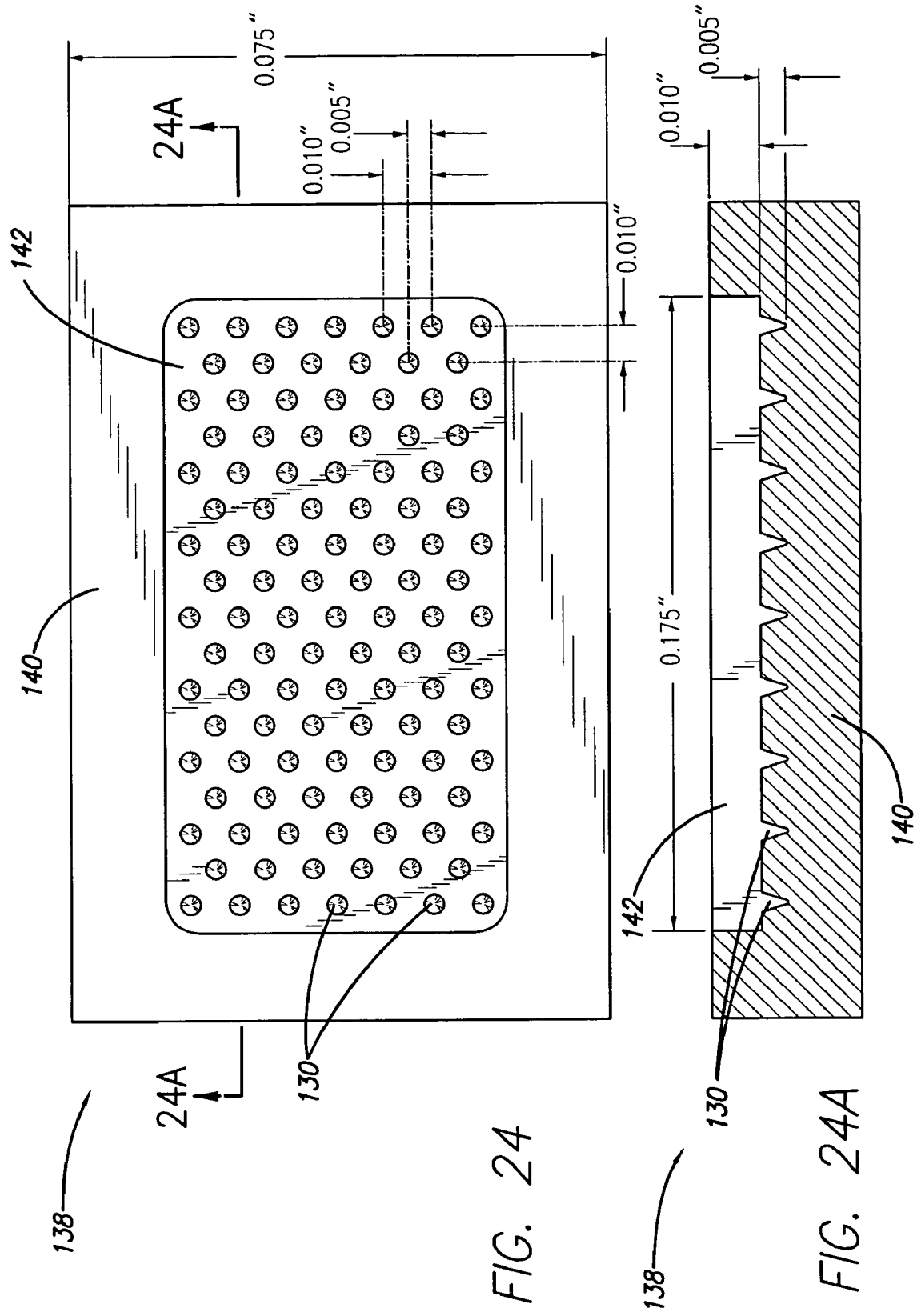

SELF-ANCHORING CARDIAC HARNESS

CROSS-REFERENCE TO RELATED APPLICATION

This application depends for priority upon U.S. Provisional Patent Application No. 60/486,062, filed Jul. 10, 2003, which is incorporated herein in its entirety by reference.

BACKGROUND OF THE INVENTION

The present invention relates to a device for treating heart failure. More specifically, the invention relates to a self-anchoring cardiac harness configured to be fit around at least a portion of a patient's heart. The cardiac harness includes an engaging element that provides a force to hold the harness onto the cardiac surface. In combination, the engaging elements hold the harness on the heart and resist migration of the harness relative to the heart during the cardiac cycle, without the need to substantially penetrate the heart.

Congestive heart failure ("CHF") is characterized by the failure of the heart to pump blood at sufficient flow rates to meet the metabolic demand of tissues, especially the demand for oxygen. One characteristic of CHF is remodeling of at least portions of a patient's heart. Remodeling involves physical change to the size, shape and thickness of the heart wall. For example, a damaged left ventricle may have some localized thinning and stretching of a portion of the myocardium. The thinned portion of the myocardium often is functionally impaired, and other portions of the myocardium attempt to compensate. As a result, the other portions of the myocardium may expand so that the stroke volume of the ventricle is maintained notwithstanding the impaired zone of the myocardium. Such expansion may cause the left ventricle to assume a somewhat spherical shape.

Cardiac remodeling often subjects the heart wall to increased wall tension or stress, which further impairs the heart's functional performance. Often, the heart wall will dilate further in order to compensate for the impairment caused by such increased stress. Thus, a cycle can result, in which dilation leads to further dilation and greater functional impairment.

Historically, congestive heart failure has been managed with a variety of drugs. Devices have also been used to improve cardiac output. For example, left ventricular assist pumps help the heart to pump blood. Multi-chamber pacing has also been employed to optimally synchronize the beating of the heart chambers to improve cardiac output. Various skeletal muscles, such as the latissimus dorsi, have been used to assist ventricular pumping. Researchers and cardiac surgeons have also experimented with prosthetic "girdles" disposed around the heart. One such design is a prosthetic "sock" or "jacket" that is wrapped around the heart.

What has been needed, and is at this time unavailable, is a cardiac harness that resists migration off of the heart without the need to apply a suture to the heart or substantially penetrate the surface of the heart.

SUMMARY OF THE INVENTION

Accordingly the present invention includes a self-anchoring cardiac harness that is configured to fit at least a portion of a patient's heart and has an engaging element for frictionally engaging an outer surface of a heart. The engaging element includes at least a surface, and may include surface relief protuberances which provide a plurality of tissue engaging elements that apply respective localized forces against the heart without substantially penetrating the heart wall. Collectively, the engaging elements produce sufficient friction relative to the outer surface so that the harness does not migrate substantially relative to the outer surface. The engaging element is formed of a material that is less compliant than the heart wall.

In one embodiment, the engaging element of a self-anchoring cardiac harness includes at least one suction cup configured to engage the heart so as to hold the harness in position on the heart. It is preferred that the harness has a plurality of spaced apart suction cups that are formed of a compliant material, such as silicone rubber.

In another embodiment of the present invention, a cardiac harness has a surface configured to engage a patient's epicardium, wherein the engaging element is at least a portion of the inner surface of the harness that has a grip portion formed of a grit. In this embodiment, the grit is a particle that can have a size between about 10-500 µm, and preferably between about 10-100 µm. The particles forming the grit can be silica or aluminum oxide particles. With a cardiac harness having a plurality of elastic rows, and wherein adjacent rows are connected by row connectors, the grit can be applied to the row connectors. In other embodiments, the grit can be applied to any portion of the harness, including the elastic rows.

In yet another embodiment, the self-anchoring harness can have an inner surface from which at least one grip protuberance extends. The grip protuberance includes a first surface portion lying generally in a first plane, a second surface portion lying generally in a second plane, and a peak along which the first and second surface portions meet, the peak defining an angle between the first and second planes. The peak is configured to engage a surface of the heart without substantially penetrating the heart surface. In one embodiment, the harness includes at least one engagement element having a plurality of grip protuberances. The engagement element can be disposed along any portion of the cardiac harness, including along elastic rows or connectors that connect adjacent rows of the harness together. In these embodiments, the grip protuberance is a polymer, such as a urethane, and the grip protuberance can be formed by injection molding.

In another embodiment, the self-anchoring cardiac harness can have at least one grip element. The grip element extends inwardly toward the heart and has a point that engages a surface of the heart without substantially penetrating the heart surface. In one embodiment, the grip element extends inwardly about 10-500 µm, and is generally conical in shape. However, the grip element may be formed into a variety of shapes, including among others, a generally pyramid-shape. A plurality of grip protuberances may be disposed on an engagement element, and the harness of the present invention may include a plurality of spaced apart engagement elements.

The present invention produces a friction by pressing an engaging element disposed on the cardiac harness against an outer surface of the heart. There is enough force created by the engaging element that there is no need to apply a suture to the heart to retain the cardiac harness. Further, the engaging elements or surface relief protuberances are adapted to engage the heart surface without substantially penetrating the heart surface.

BRIEF DESCRIPTION OF THE DRAWINGS

FIG. 14A depicts a partial cross-section of the tissue engaging element taken along line 14A-14A of FIG. 14.

FIG. 15 depicts an enlarged view of yet another embodiment of a tissue engaging element having surface relief protuberances.

FIG. 15A depicts a partial cross-section of the tissue engaging element taken along line 15A-15A of FIG. 15.

FIG. 16 depicts an enlarged view of another embodiment of a tissue engaging element having surface relief protuberances.

FIG. 16A depicts a partial cross-section of the tissue engaging element taken along line 16A-16A of FIG. 16.

FIG. 17 depicts an enlarged view of yet another embodiment of a tissue engaging element having surface relief protuberances.

FIG. 17A depicts a partial cross-section of the tissue engaging element taken along line 17A-17A of FIG. 17.

FIG. 23A depicts a plan view of an embodiment of a tissue engaging element having conical protuberances spaced apart from one another.

FIG. 23B depicts a cross-sectional view of the tissue engaging element taken along line 23B-23B of FIG. 23A.

FIG. 24 depicts a plan view of a mold for forming an array of conical protuberances.

FIG. 24A depicts a cross-sectional view of the mold taken along line 24A-24A of FIG. 24.

DETAILED DESCRIPTION OF THE PREFERRED EMBODIMENTS

This invention relates to a method and apparatus for treating heart failure. As discussed in Applicants' co-pending application entitled "Expandable Cardiac Harness For Treating Congestive Heart Failure", Ser. No. 09/634,043, which was filed on Aug. 8, 2000, the entirety of which is hereby expressly incorporated by reference herein, it is anticipated that remodeling of a diseased heart can be resisted or even reversed by alleviating the wall stresses in such a heart. The present application discusses certain embodiments and methods for supporting the cardiac wall. Additional embodiments and aspects are also discussed in Applicants' co-pending applications entitled "Device for Treating Heart Failure," Ser. No. 10/242,016, filed Sep. 10, 2002; "Heart Failure Treatment Device and Method", Ser. No. 10/287,723, filed Oct. 31, 2002; "Method and Apparatus for Supporting a Heart", Ser. No. 10/338,934, filed Jan. 7, 2003; and "Method and Apparatus for Treating Heart Failure," Ser. No. 60/409,113, filed Sep. 5, 2002; "Cardiac Harness Delivery Device and Method," Ser. No. 60/427,079, filed Nov. 15, 2002; and "Multi-panel Cardiac Harness, Ser. No. 60/458,991, filed Mar. 28, 2003, the entirety of each of which is hereby expressly incorporated by reference.

Figure 1:
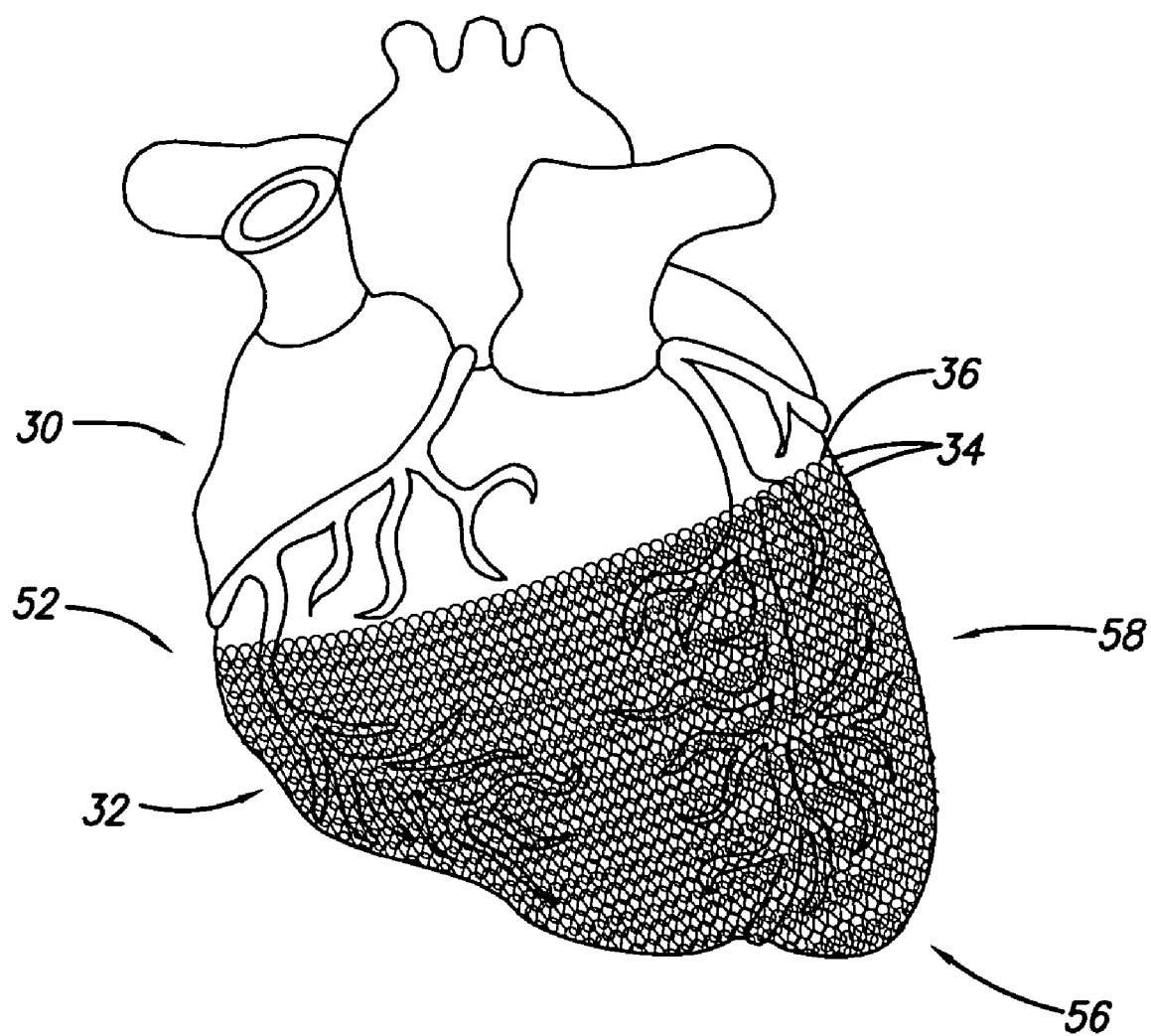
FIG. 1 depicts a schematic view of a heart with a prior art cardiac harness placed thereon.

FIG. 1 illustrates a mammalian heart 30 having a prior art cardiac wall stress reduction device in the form of a harness 32 applied to it. The cardiac harness has rows 34 of elastic members 36 that circumscribe the heart and, collectively, apply a mild compressive force on the heart so as to alleviate wall stresses.

The term "cardiac harness" as used herein is a broad term that refers to a device fit onto a patient's heart to apply a compressive force on the heart during at least a portion of the cardiac cycle. A device that is intended to be fit onto and reinforce a heart and which may be referred to in the art as a "girdle," "sock," "jacket," "cardiac reinforcement device," or the like is included within the meaning of "cardiac harness."

Figure 2A:
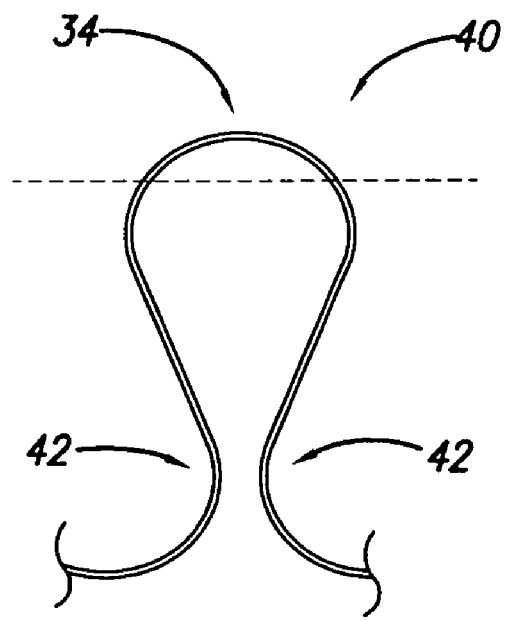
FIGS. 2A-2B depict a spring hinge of a prior art cardiac harness in a relaxed position and under tension.
Figure 2B:
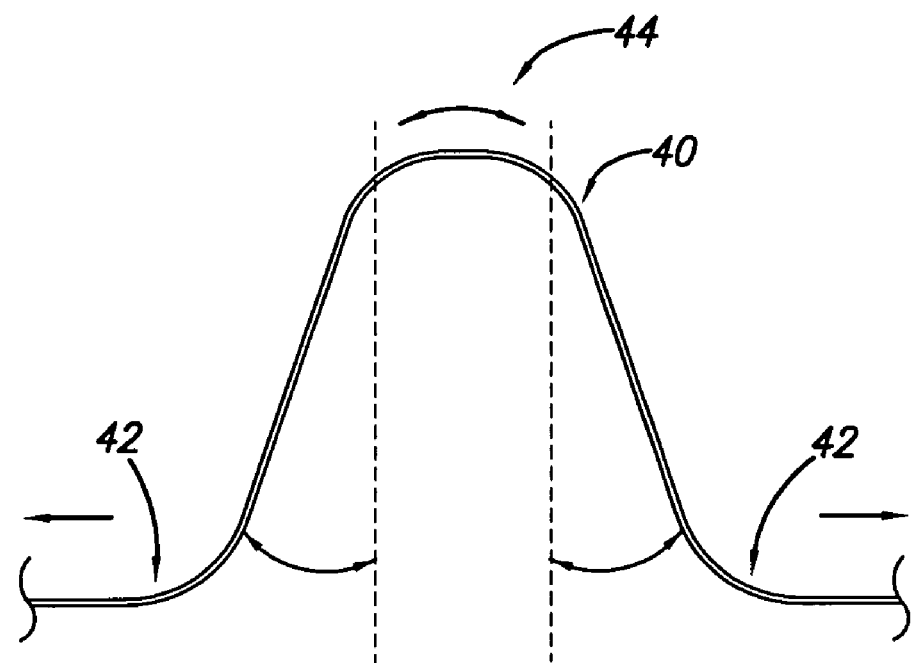

The cardiac harness 32 illustrated in FIG. 1 has several rows 34 of elastic members 36. Each row includes a series of spring elements, referred to as hinges, or spring hinges, that are configured to deform as the heart 30 expands during filling. For example, FIG. 2A shows a prior art hinge member 36 at rest. The hinge member has a central portion 40 and a pair of arms 42. As the arms are pulled, as shown in FIG. 2B, a bending moment 44 is imposed on the central portion. The bending moment urges the hinge member back to its relaxed condition. Note that a typical row or strand comprises a series of such hinges, and that the hinges are adapted to elastically expand and retract in the direction of the strand.

In the harness illustrated in FIG. 1, the elastic rows 34 are constructed of drawn wire that is deformed to form the spring elements 36.

Figure 3:
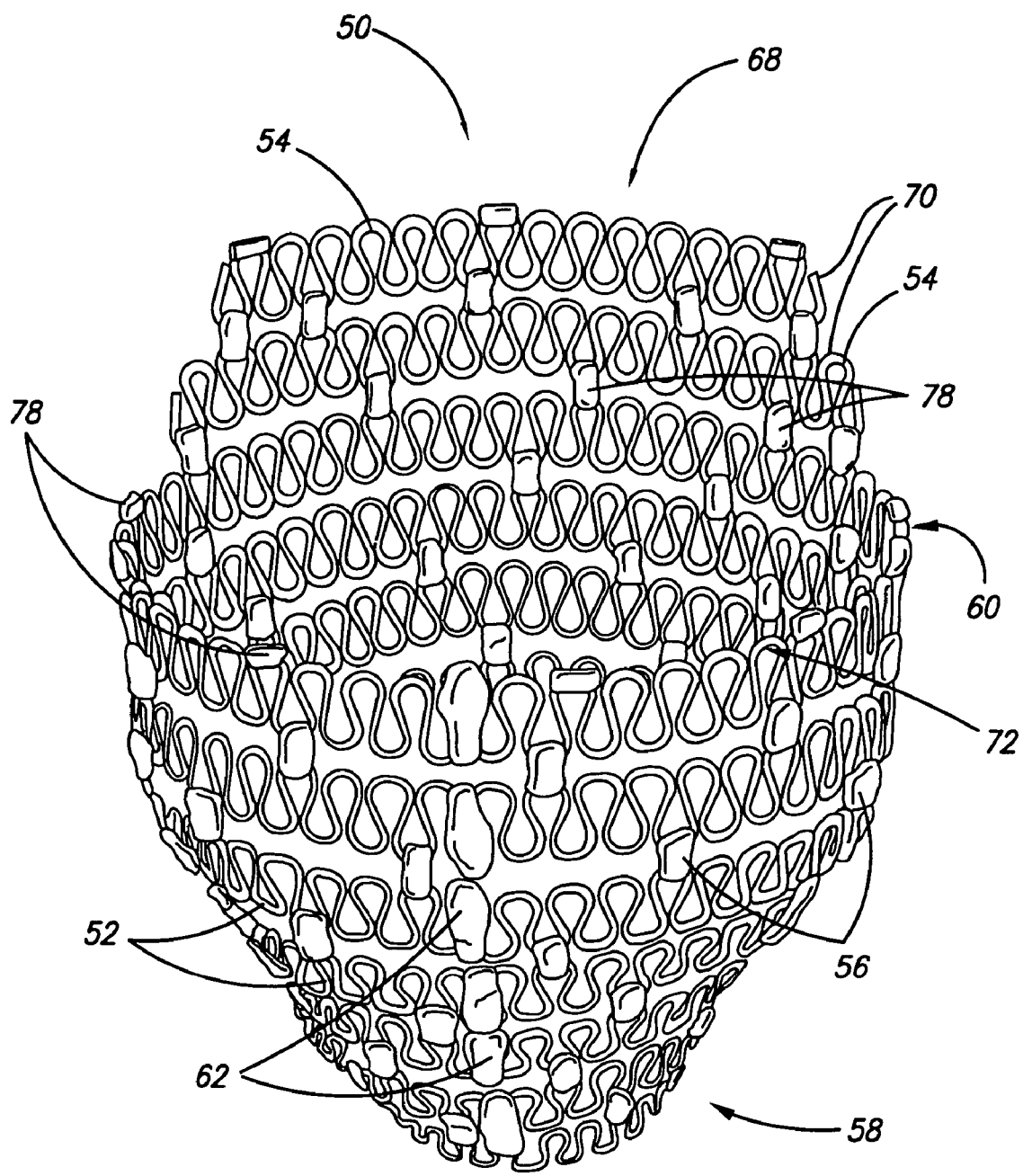
FIG. 3 depicts a perspective view of one embodiment of a cardiac harness having a plurality of rings, and tissue engaging elements disposed along the rings.

In one embodiment of the invention, as shown in FIG. 3, a cardiac harness 50 has several adjacent elastic rows 52 of spring members 54 is illustrated. In this embodiment, adjacent rows preferably are connected to one another by one or more connectors 56. The connectors help maintain the position of the elastic rows relative to one another. Preferably, the connectors have a length oriented longitudinally relative to the elastic rows so as to create a space between adjacent rows. The illustrated harness is configured to circumferentially surround at least a portion of the heart between an apex portion 58 and a base portion 60. Preferably, the connectors allow some relative movement between adjacent rows.

The connectors 56 preferably are formed of a semi-compliant material such as silicone rubber. Most preferably the connectors are formed of the same material used for coating the rings with a dielectric coating, if applicable. Some materials that can be used for the connectors include, for example, medical grade polymers such as, but not limited to, polyethylene, polypropylene, polyurethane and nylon.

As discussed above, and as discussed in more detail in the applications that are incorporated herein by reference, the elastic rows 52 exert a force in resistance to expansion of the heart. Collectively, the force exerted by the elastic rows tends toward compressing the heart, thus alleviating wall stresses in the heart as the heart expands. Accordingly, the harness helps to decrease the workload of the heart, enabling the heart to more effectively pump blood through the patient's body and enabling the heart an opportunity to heal itself. It should be understood that several arrangements and configurations of elastic rows can be used to create a mildly compressive force on the heart so as to reduce wall stresses. For example, elastic members 54 can be disposed over only a portion of the circumference of the heart or harness.

Figure 4:
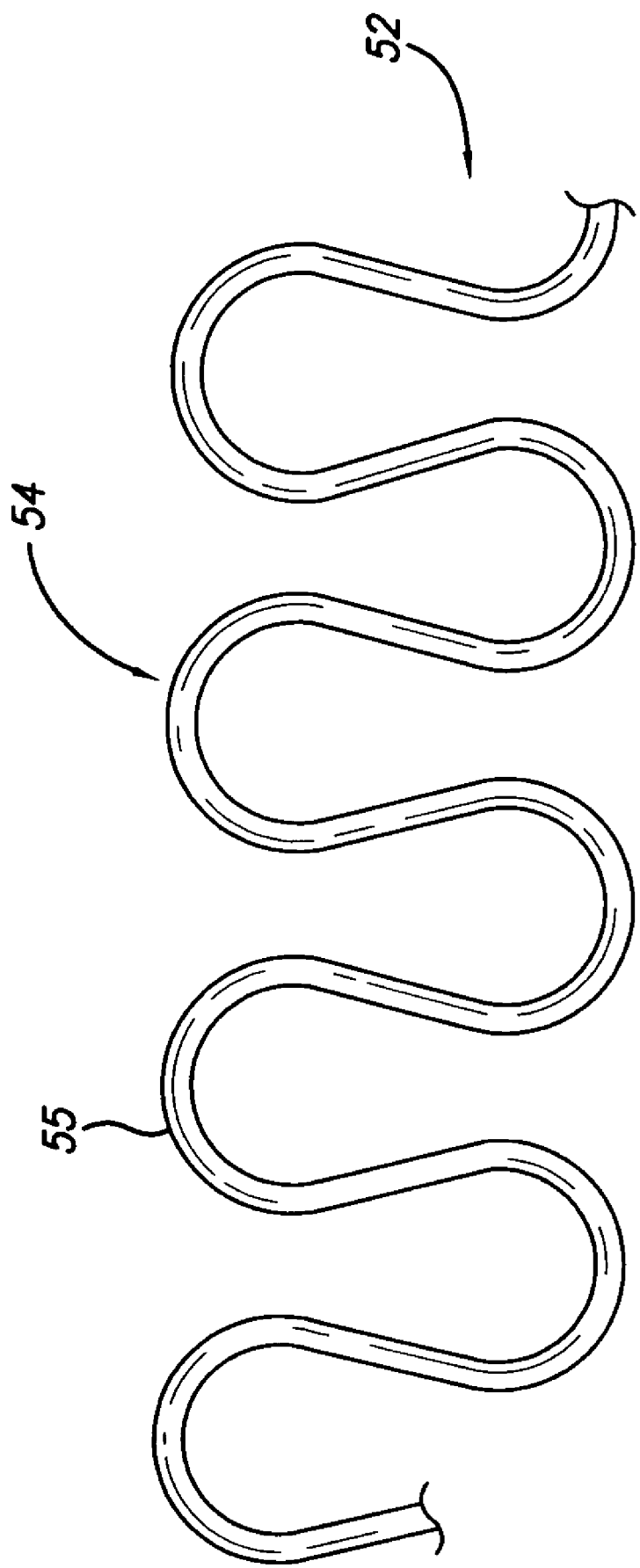
FIG. 4 depicts an unattached elongated strand or series of spring elements that are coated with a dielectric material.

With next reference to FIG. 4, a close-up of a portion of one embodiment of an elastic row 52 is shown. In the illustrated embodiment, the row has an undulating strand of drawn wire formed into a series of successive spring elements 54. A dielectric coating 55 is disposed over the spring elements to electrically insulate the strand of drawn wire. In the illustrated embodiment, the dielectric coating includes silicone rubber. Other acceptable materials include urethanes as well as various polymers, elastomers and the like. In the illustrated embodiment, the silicone rubber coating is a tubing that has been pulled over the wire. It is to be understood that other methods for applying a coating, such as dip coating and spraying, can also be used to apply a coating to the elastic row. Further, it should be understood that in other embodiments no coating is applied over the elastic row.

In one embodiment, each elastic row 52 initially includes an elongate strand. During manufacturing of the cardiac harness 50, each elongate strand is cut to a length such that when opposite ends of the elongate strand are bonded together, the elongate strand assumes a ring-shaped configuration. The rings form the adjacent elastic rows. The lengths of the elongate strands are selected such that the resulting rings/rows are sized in conformity with the general anatomy of the patient's heart. More specifically, strands used to form the apex portion 58 of the harness are not as long as strands used to form the base portion 60. As such, the harness generally tapers from the base toward the apex in order to generally follow the shape of the patient's heart.

In another embodiment, the diameter of a ring at the base of the harness is smaller than the diameter of the adjacent ring. In this embodiment, the harness has a greatest diameter at a point between the base and apex ends, and tapers from that point to both the base and apex ends. Preferably, the point of greatest diameter is closer to the base end than to the apex end. It is contemplated that the lengths of the strands, as well as the sizes of the spring members, may be selected according to the intended size of the cardiac harness and/or the amount of compressive force the harness is intended to impart to the patient's heart.

Figure 5:
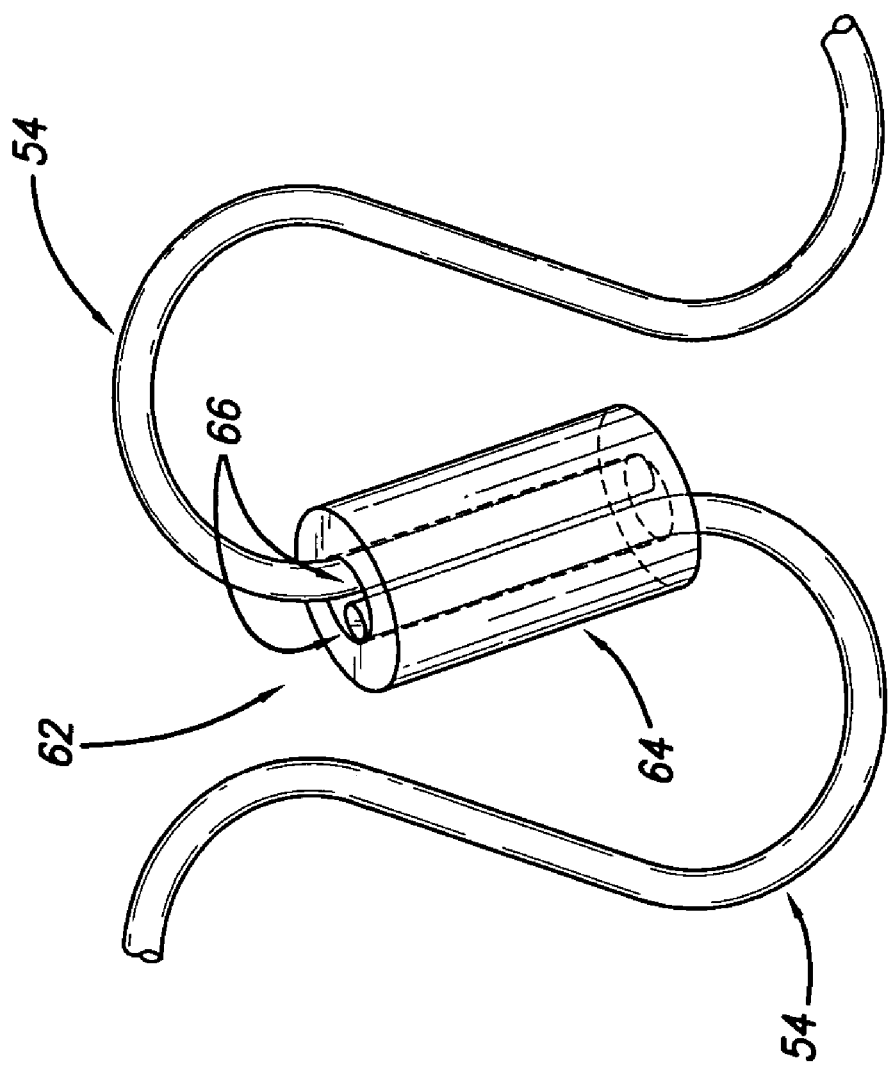
FIG. 5 depicts a partial cross-sectional view of opposite ends of a ring attached to one another by a connective junction.

With continued reference to FIG. 3, the opposite ends of each circumferentially extending ring 52 are attached to one another by a connective junction 62. In one embodiment, illustrated in FIG. 5, each connective junction includes a small tube segment 64 into which opposite ends 66 of the ring are inserted. The tube segment serves to prevent the opposite ends of the ring from tearing loose from one another after the harness is placed on the heart. Preferably, each tube segment is filled with a dielectric material such as silicone rubber or another similar material after the ring-ends are placed therein. It is to be understood that additional methods and structure can be used to form the connective junctures. For example, the ends of the strands can be welded together or intertwined. Also, in other embodiments, each ring can be unitarily formed, such as by molding, without requiring cutting and joining of the ends.

In a human heart the right ventricle extends further from the apex of the heart than does the left ventricle. The cardiac harness 50 illustrated in FIG. 3 has a right ventricle engagement portion 68 configured to fit about the uppermost portion of the right ventricle where the ventricle begins to curve inwardly. With continued reference to FIG. 3, the right ventricle engagement portion of the harness has elastic rows that form only a partial circle. Preferably, these partial rings 70 are connected to the adjacent full ring in a manner so that the partial rings are at least mildly stretched when the rest of the harness is at rest. As such, the partial strands are biased inwardly. When placed on the heart, the partial rings "cup" the upper portion of the right ventricle. As such, the harness fits better and is held more securely on the heart than if the right side of the harness were configured the same as the left side.

In yet another embodiment, a cardiac harness has a basal-most ring 72 that is less compliant than rings elsewhere in the harness. In one embodiment, the basal-most ring has a larger diameter wire than the wire comprising the other rings of the harness. In another embodiment, the basal-most ring has a shorter length of wire than the other rings of the harness. As such, once the cardiac harness is appropriately positioned on the heart, the basal-most ring tightly engages the heart and resists apical migration of the harness. The basal-most region of the ventricles adjacent to the AV groove undergoes less circumferential change during a cardiac cycle than does the remaining bulk of the ventricles. As such, it is contemplated that the basal-most ring will have minimal or no adverse impact on cardiac performance, or cardiac cycle dynamics. It is also to be understood that, in other embodiments, multiple rings, or a basal-most portion of the harness, may have the reduced compliance. Such reduced compliance may be obtained in any manner. For example, in one embodiment, the basal-most portion is pre-stretched relative to the rest of the harness. In another embodiment, the basal-most portion is formed of a thicker or different material than other portions of the harness.

It is to be understood that several embodiments of cardiac harnesses can be constructed and that such embodiments may have varying configurations, sizes, flexibilities, etc. As discussed in the above-referenced applications, such harnesses can be constructed from many suitable materials including various metals, woven or knitted fabrics, polymers, plastics and braided filaments, and may or may not include elastic rows. Suitable harness materials also include superelastic materials and materials that exhibit shape memory. For example, a preferred embodiment is constructed of Nitinol. Shape memory polymers can also be employed. Such shape memory polymers can include shape memory polyurethanes or other polymers such as those containing oligo(e-caprolactone) dimethacrylate and/or poly (e-caprolactone), which are available from mnemoScience. Further, harness materials can be elastic or substantially non-elastic.

Figure 6:
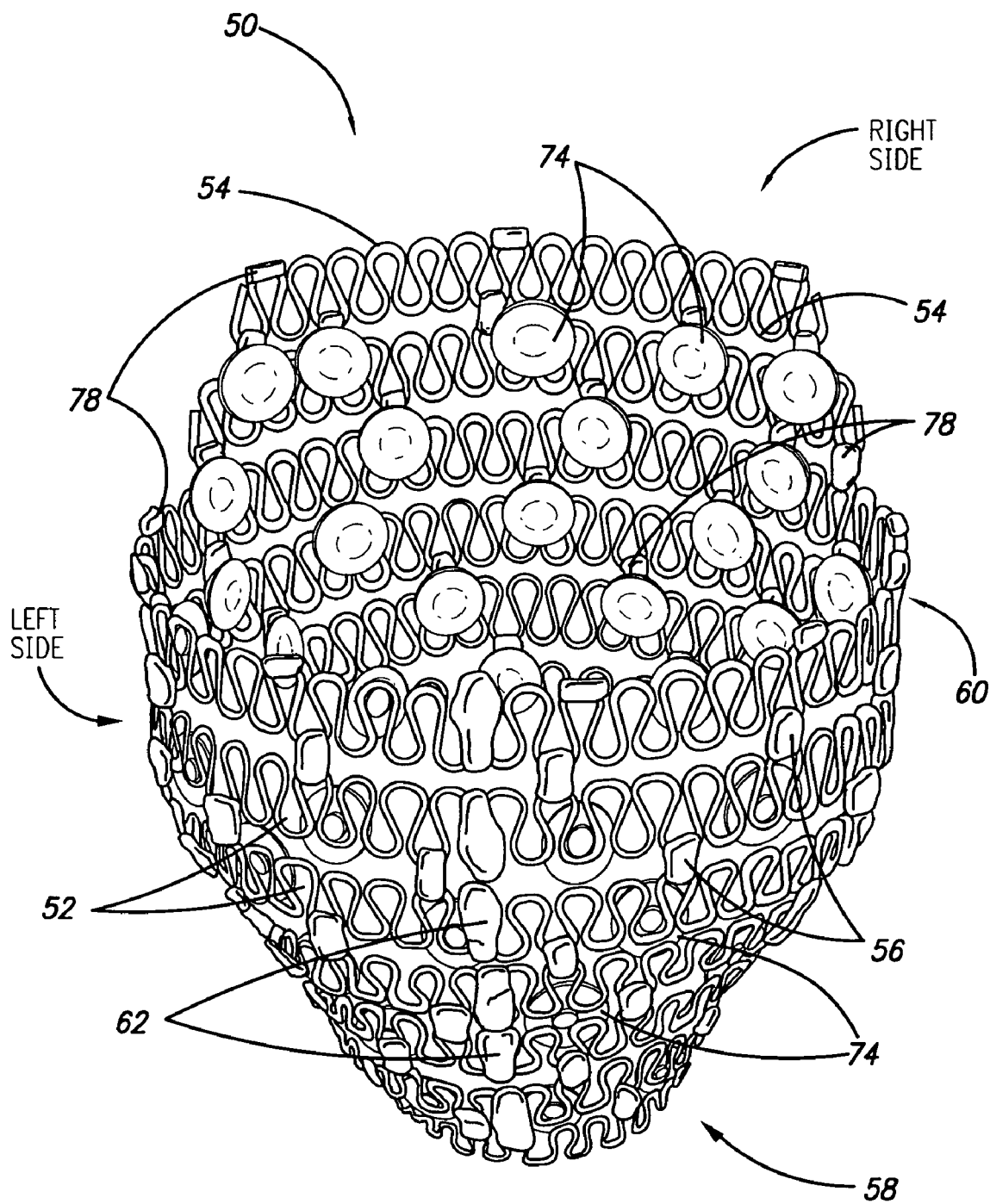
FIG. 6 depicts a perspective view of another embodiment of a cardiac harness having a plurality of rings, and suction cups disposed along the inner surface of the harness.

With next reference to FIG. 6, another embodiment of a cardiac harness 50 is illustrated. The illustrated harness has several inwardly-directed suction cups 74 extending from an inner surface of the harness. As shown in the illustrated embodiment, the suction cups are spaced apart from each other. Each cup is configured to engage the outer surface of the heart to create a local engagement force holding the harness onto the cardiac surface. The combined action of the several local engagement forces combine to hold the harness on the heart so as to resist migration of the harness relative to the heart during the cardiac cycle. As such, the illustrated harness embodiment anchors itself to the heart. Other embodiments of tissue engagement elements as will be described below, may also be used in conjunction with the suction cups to anchor the harness onto the heart.

In the illustrated embodiment shown in FIG. 6, the suction cups 74 may be disposed on the connectors 56 between elastic rows 52. It is to be understood, however, that in additional embodiments, suction cups can extend inwardly from any portion of the harness. In one embodiment, the suction cups are co-formed with the harness. In another embodiment, the suction cups are formed separately from the harness and are attached to the harness.

In accordance with another embodiment, a cardiac harness 50 having a structure similar to the embodiment shown and described in connection with FIG. 3 further includes a textured coating including particles or grit 76 having sizes measurable on the order of microns. As such, when the harness is disposed on the heart, and the harness gently squeezes the heart, the grit engages the heart surface so as to resist migration of the harness relative to the heart surface during the cardiac cycle.

Figure 7:
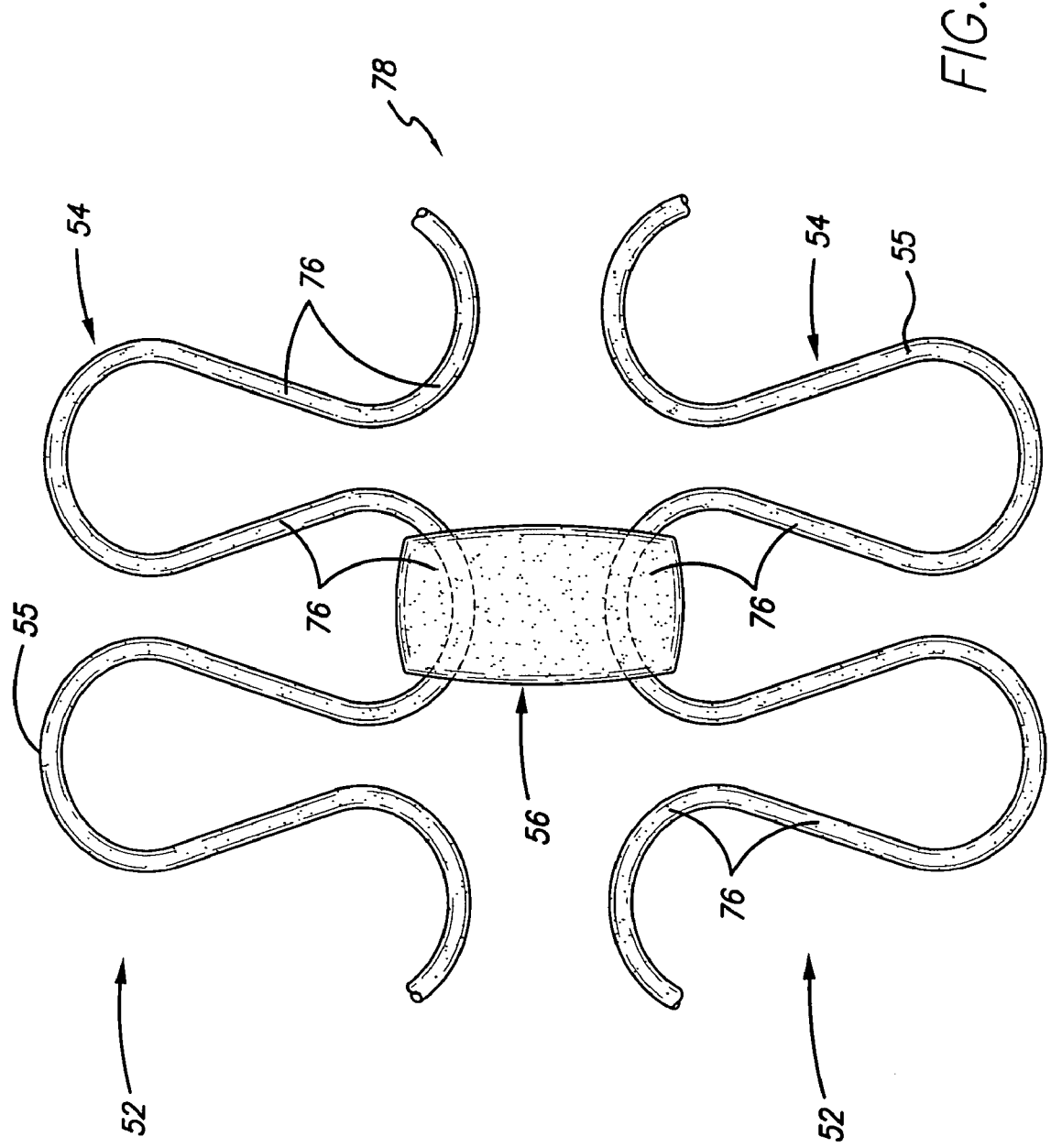
FIG. 7 depicts an enlarged partial plan view of a cardiac harness having grit disposed on the entire inner surface of the harness, including the rings of the harness and a connector that joins adjacent rings together.

FIG. 7 is a close up view of a portion of the inner surface of a cardiac harness embodiment having a structure in accordance with this aspect. As depicted in FIG. 7, grit 76 is distributed generally around the entire inner surface of the harness. The grit may be applied to the harness in accordance with various methods such as spray coating, dipping, or the like. In the illustrated embodiment, the grit is attached to the dielectric coating 55 of the undulating wire. It is to be understood that in additional embodiments grit can be adhered directly to any structure on the inner surface of the harness.

In a preferred embodiment, a grit 76 having a size between about 10 to 500 micrometers is used. Each particle of grit, when engaged with the heart surface, creates a localized friction force that resists migration of the grit and associated harness relative to the heart surface. The several localized forces generated by each grit particle interacting with the heart surface collectively comprise a harness friction force which resists migration of the harness relative to the heart surface.

Although the grit 76 engages the heart surface and/or tissue adjacent the heart surface, it does not substantially penetrate the heart surface due to the small size of the grit particles. This should be taken to mean that the grit engaging the heart surface does not penetrate the heart surface sufficiently to cause any debilitating injury to the heart. Further, the grit does not penetrate the tissue enough to puncture any coronary vessel wall.

As discussed above, the grit 76 preferably extends from the inner wall of the cardiac harness. As such, each particle of grit includes a protuberance extending from the harness. Collectively, several particles of grit create a three-dimensional surface relief that is relatively rough and which, when engaged with the heart surface, creates a friction force that resists migration of the harness relative to the heart.

Multiple particles of grit 76, taken together, make up a tissue engagement element 78. In the embodiment illustrated in FIG. 7, since the grit is disposed generally evenly throughout the inner surface of the harness, the entire inner surface can be considered a tissue engaging element, or a certain zone or portion of the grit-covered inner surface can be defined as a tissue engagement element.

In accordance with another embodiment, a cardiac harness has a plurality of tissue engaging elements 78. Each tissue engaging element includes a surface relief made up of a plurality of protuberances. In this embodiment, surface relief protuberances are collected in tissue engaging elements, and substantially no surface relief protuberances are provided on the inner surface of the harness between tissue engagement elements, which are spaced apart from one another.

Figure 8:
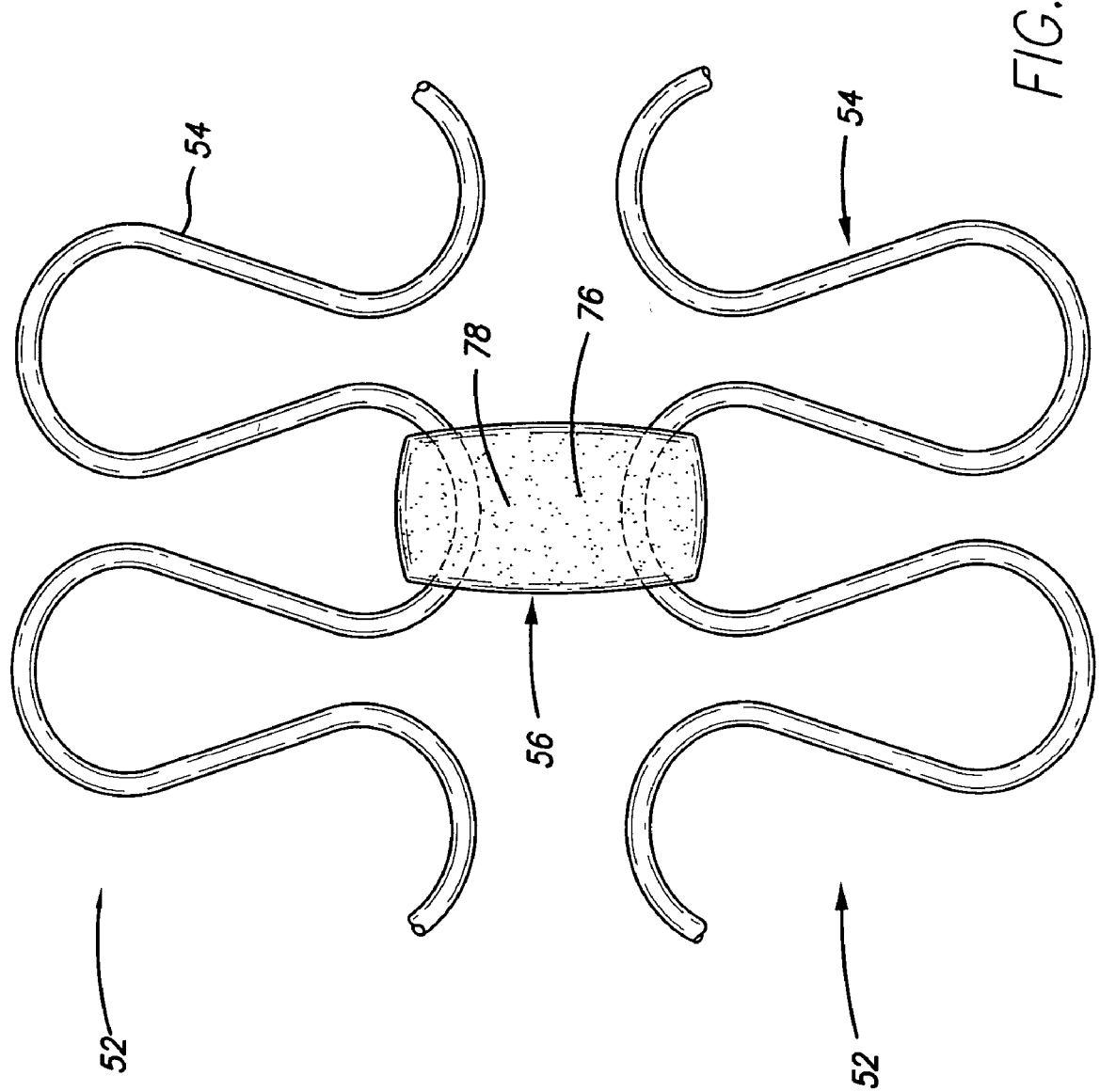
FIG. 8 depicts an enlarged partial plan view of a cardiac harness having grit disposed only on a connector that joins adjacent rings together, and not on the rings of the harness.

FIG. 8 shows a portion of a harness having a structure similar to the harness shown and discussed in connection with FIG. 3, wherein a plurality of tissue engagement elements 78, each having surface relief protuberances, are disposed on the inner surface of the harness and spaced apart from one another. In the illustrated embodiment, the tissue engagement elements have grit particles 76 having sizes of about 50 to 500 micrometers. More preferably the grit particles are between about 50 to 250 micrometers, still more preferably between about 60 to 200 micrometers, and most preferably between about 50 to 100 micrometers. In another embodiment, the particles are between about 200 to 400 micrometers. In a still further embodiment the grit has a medium grit of about 220 mesh. As discussed above, the grit particles have protuberances that collectively create a surface relief so that each tissue engaging element applies a localized frictional force between the heart surface and the harness in order to resist migration of the harness relative to the surface.

In the embodiments discussed above, the particles of grit preferably are sufficiently hard to engage the heart wall without bending. As such, the surface relief protuberances will firmly engage the heart wall. In a preferred embodiment, such surface relief protuberances are less compliant than the heart wall in order to ensure a thorough and firm engagement.

The grit particles 76 in the above embodiments can include any of several materials. In accordance with one embodiment, the grit particles comprise 66 μm aluminum oxide. It is to be understood that several other materials can be used. Preferably such materials include a bio-compatible material such as silica or other similarly textured materials. In another embodiment, the grit particles are biodegradable materials such as, for example, calcium sulfate, hydroxyapatite, polymethlmethacrylate (PMMA), polylactic acid (PLA), polyglycolic acid (PGA), or the like.

Figure 9:
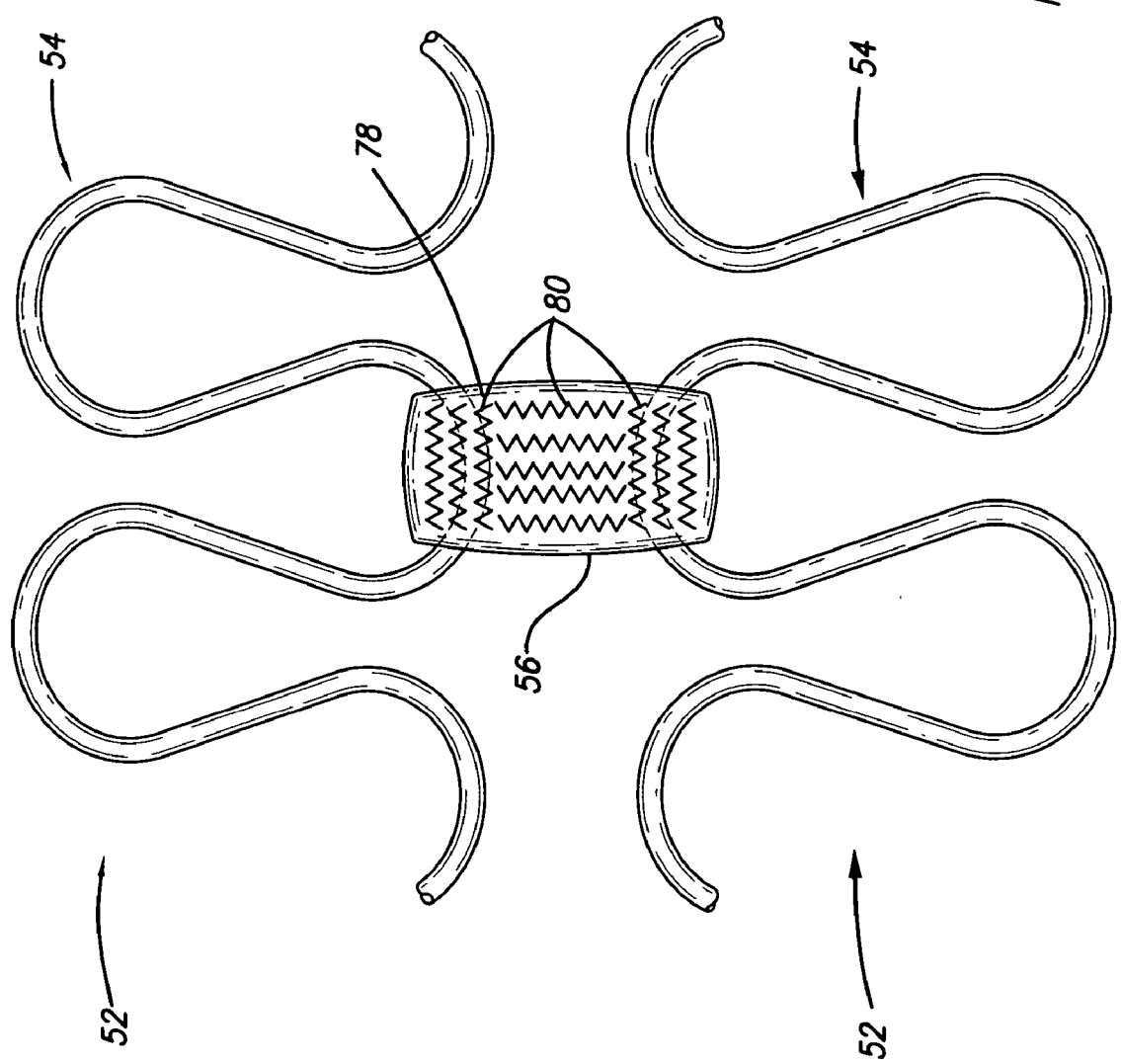
FIG. 9 depicts an enlarged partial plan view of a cardiac harness wherein the connector is a tissue engaging element having surface relief protuberances disposed thereon.

With next reference to FIG. 9, another embodiment of a cardiac harness 50 has tissue engagement elements 78 that include surface relief protuberances 80. In the illustrated embodiment, the tissue engagement element is disposed on a connector 56 between elastic rows 52. As discussed above, such connectors preferably are formed of a semi-compliant material such as, for example, silicone or urethane. In the illustrated embodiment, the inner surface of the silicone rubber connector is treated chemically in order to alter its properties, and to create surface relief protuberances that will increase the frictional force resisting relative movement between the connector and the heart surface. In accordance with one embodiment, plasma modification is used to change the cross-linking properties of the surface of the connector in order to form the tissue engaging element having surface relief protuberances. In another embodiment, other chemical processes are used to harden the surface. In another embodiment, the surface of the connector is coated with a ceramic deposition to create surface relief protuberances. In yet another embodiment, the connector is mechanically roughened such as by sanding, machining or the like in order to create surface relief protuberances. In a still further embodiment, after surface relief protuberances are formed on a connector, the surface of the connector is chemically or mechanically treated to harden the surface of the connector so that the surface relief protuberances are sufficiently rigid to engage the heart surface.

Figure 10:
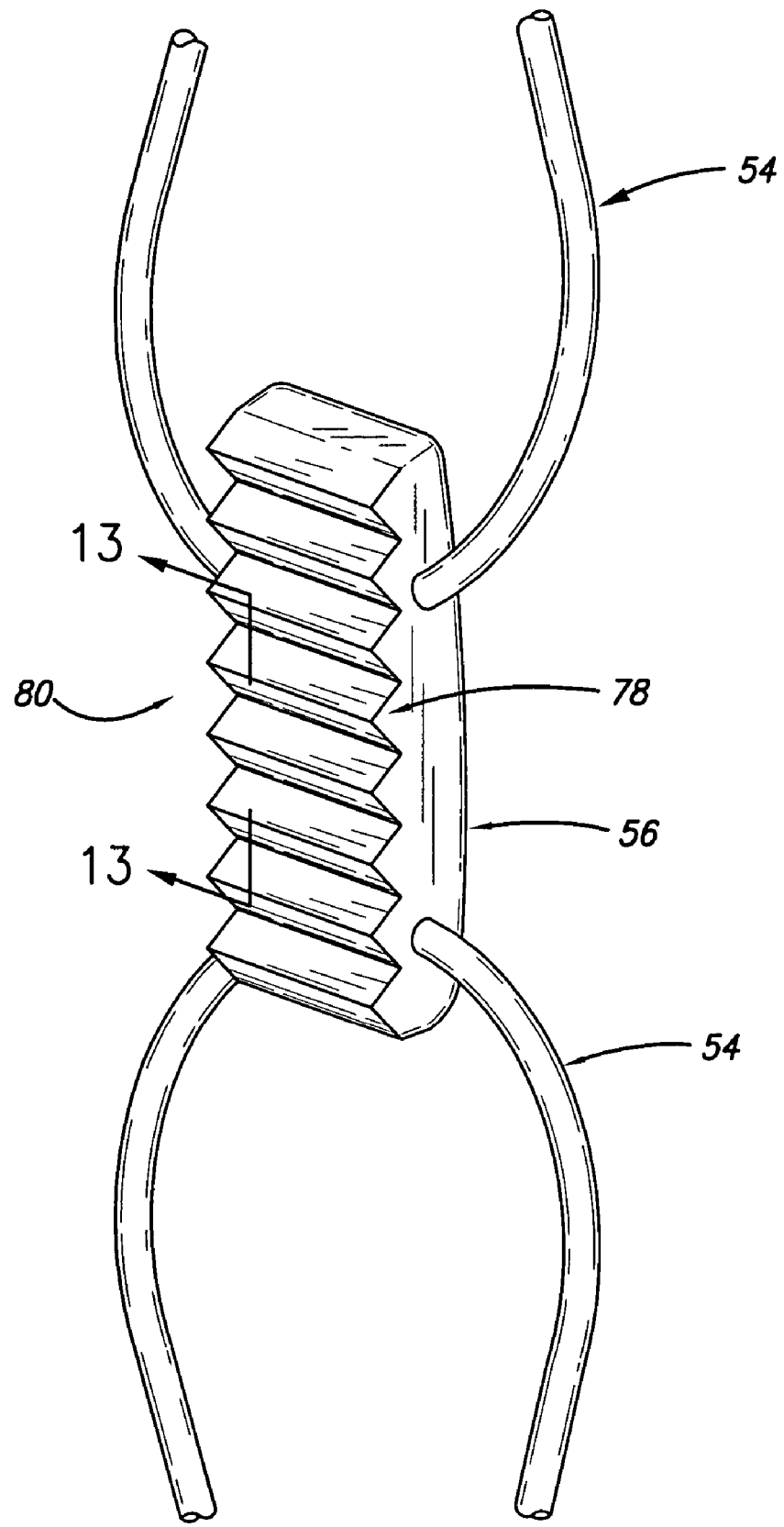
FIG. 10 depicts an enlarged view of another embodiment of a tissue engaging element having surface relief protuberances.
Figure 11:
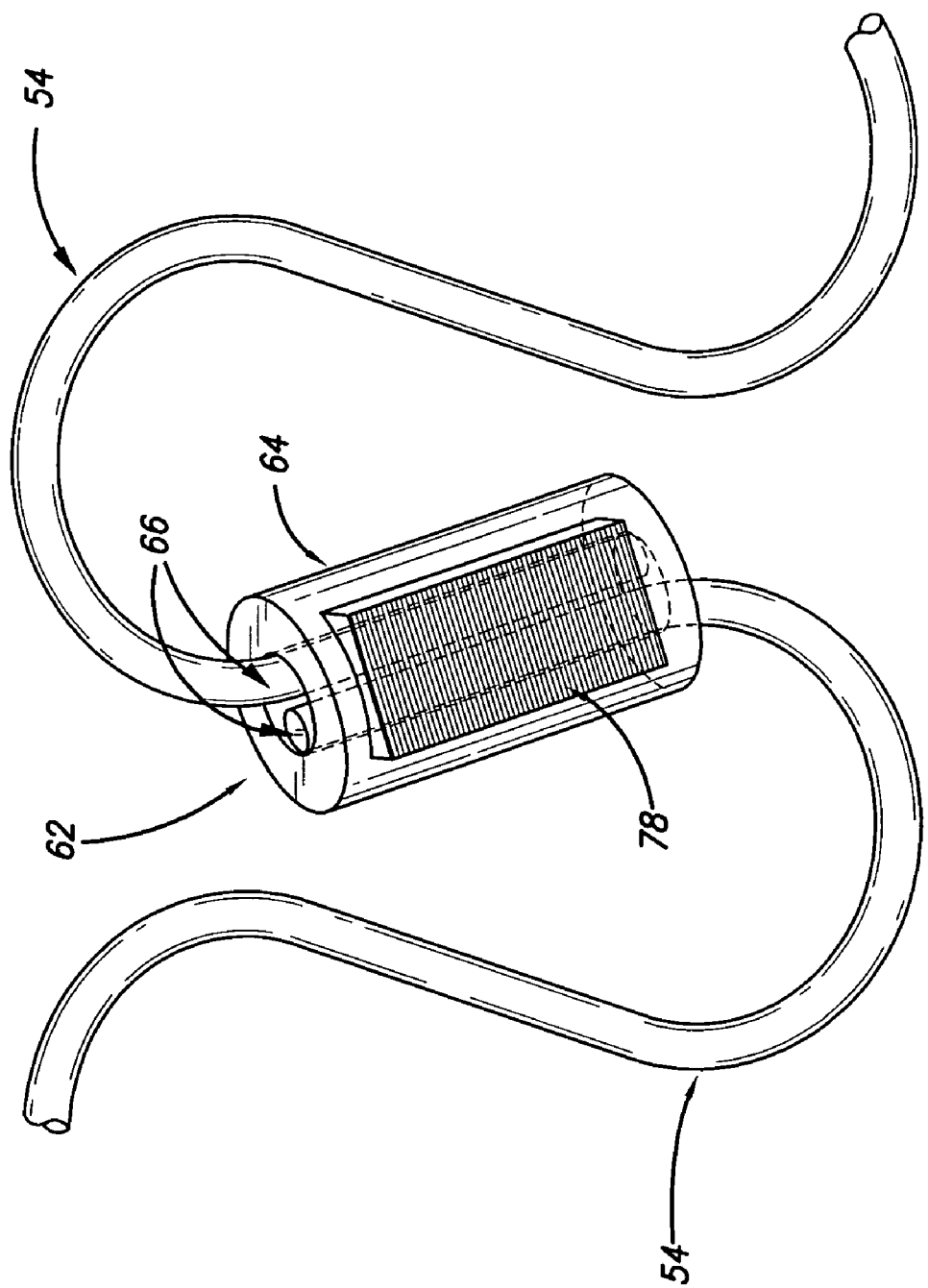
FIG. 11 depicts a partial cross-sectional view of opposite ends of a ring attached to one another by a connective junction and a tissue engaging element disposed on the connective junction.
Figure 12:
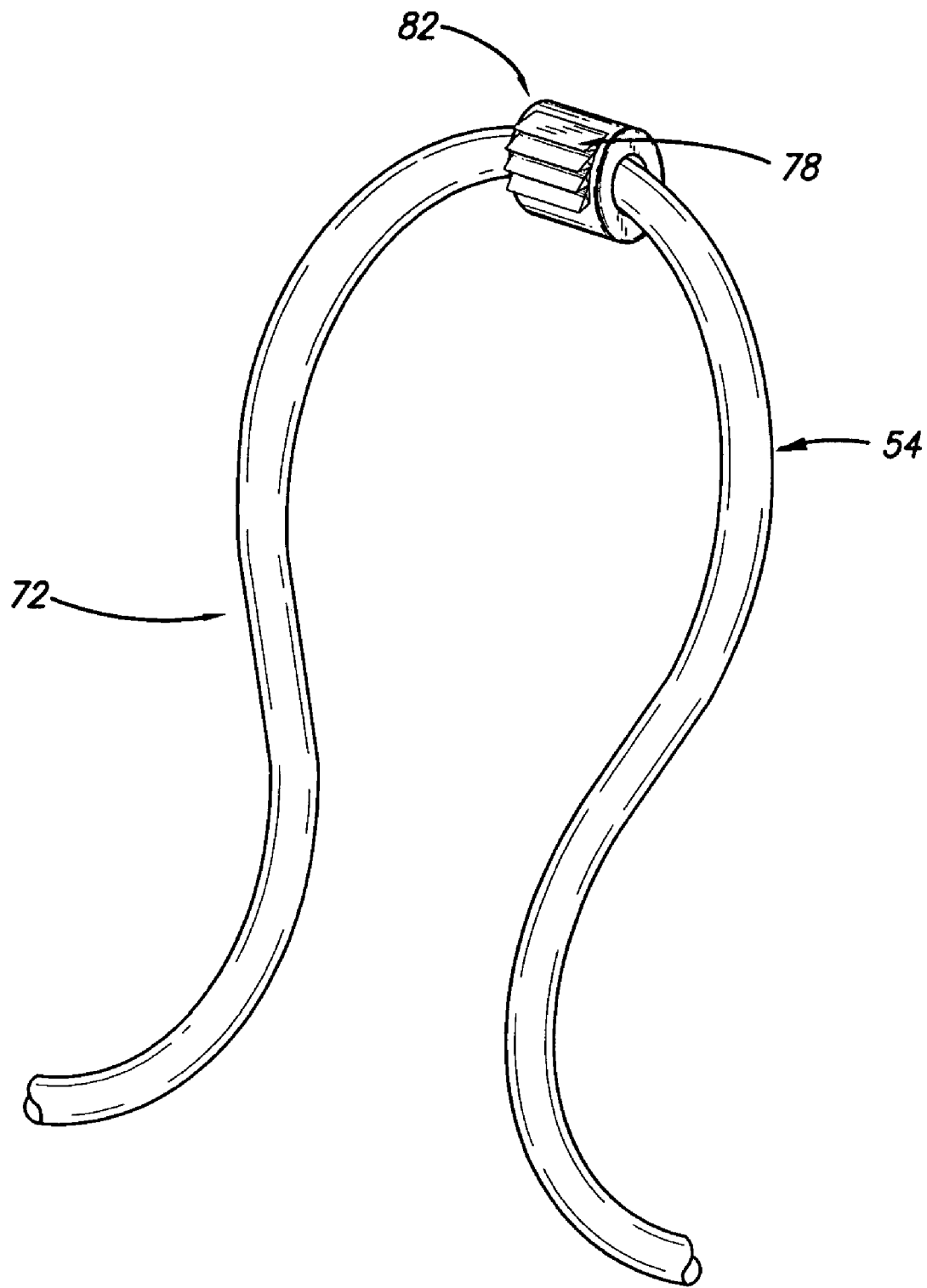
FIG. 12 depicts an enlarged view of another embodiment of a tissue engaging element disposed on a tube segment that is attached to a spring member of the cardiac harness.

With reference next to FIG. 10, a close-up view is provided of another embodiment wherein a tissue engaging element 78 has surface relief protuberances 80 that are manufactured according to a prescribed pattern. In the illustrated embodiment, the tissue-engaging element is located on a connector 56 disposed between adjacent elastic rows 52 in an embodiment of a harness having a structure similar to that shown and described in connection with FIG. 3. With reference next to FIG. 11, in accordance with another embodiment, a tissue-engaging element 78 is disposed on a connective junction 62 of a harness. With reference next to FIG. 12, in accordance with still another embodiment, a tissue-engaging element 78 is disposed on a tube segment 82 at a basal-most ring 72 and at an upper-most portion of a harness. Each of the embodiments shown in FIGS. 10 through 12 show different arrangements of tissue-engaging elements that can be used for a harness having structure similar to that shown and described in connection with FIG. 3. It is to be understood, however, that tissue-engaging elements can be used with any cardiac harness having any type of structure.

As just discussed, an embodiment of a tissue engaging element 78 has a manufactured pattern that defines surface relief protuberances 80. It should be appreciated that several such patterns, as well as several methods and apparatus for constructing such patterns, can be employed. The discussion below presents some additional examples of tissue engaging elements.

Figure 13:
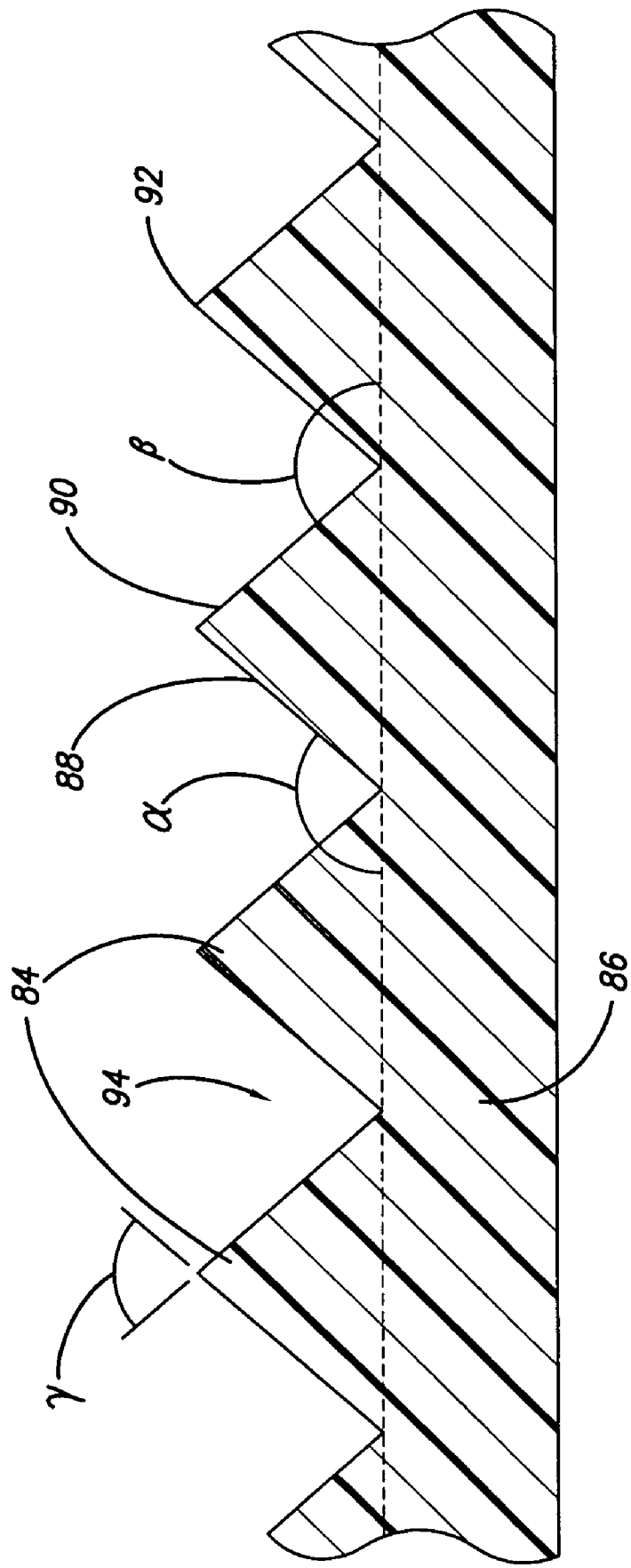
FIG. 13 depicts a partial cross-section taken along line 13-13 of FIG. 10, showing the engagement element having a surface relief formed by several rows of elongated protuberances extending from a substrate.

With reference again to FIG. 10 and also to FIG. 13, which is a partial cross-section of FIG. 10 taken along line 13-13, the engagement element 78 has a surface relief 80 formed by several rows of elongate protuberances 84. The protuberances extend from a substrate 86 of the engagement element. Each protuberance has a first planar surface 88 and a second planar surface 90 that intersect along an edge 91. In the illustrated embodiment, the edge also has a peak 92, which is the furthest-most point from the substrate of the engagement element. As there are several rows of protuberances, there is a space 94 between adjacent protuberance peaks.

The first planar surface 88 is disposed at a first angle $\alpha$ relative to a tangent or plane of the substrate 86. The first angle is measured from the open face of the first surface to the substrate. The second planar surface 90 is disposed at a second angle $\beta$. An edge or peak angle $\gamma$ is defined by the intersection of the first and second planar surfaces. In the illustrated embodiment, the first and second angles are generally the same, about 135°, and the peak angle is about 90°. Of course, in other embodiments, the first and second angles are not necessarily the same, and one of the angles can be acute. Further, in other embodiments the peak angle can be acute or obtuse.

In accordance with this embodiment, the tissue engagement element 78 is configured so that the protuberances 84 engage the heart surface. Preferably, the size and peak angles $\gamma$ of the protuberances are configured so that they engage heart tissue without substantially penetrating the heart surface, but also create a friction force that will resist migration of the engagement element relative to the heart surface in at least a direction generally transverse to the edge of the protuberances.

In accordance with one embodiment, material is drawn in the shape of the tissue engagement element embodiment discussed above. The drawn material is then cut to the size and shape of the engagement element 78 shown in FIG. 10. The engagement element is then bonded or otherwise attached to the harness. In the illustrated embodiment, the engagement element is bonded to a connector 56 disposed between adjacent elastic rows 52. It is to be understood that, in other embodiments, the engagement element can be adhered or otherwise attached to any portion of a cardiac harness. Additionally, in accordance with other embodiments, an engagement element can be molded, machined or otherwise formed. Further, an engagement element can be attached to a connector, or an engagement element can be co-formed as part of a connector.

Figure 14:
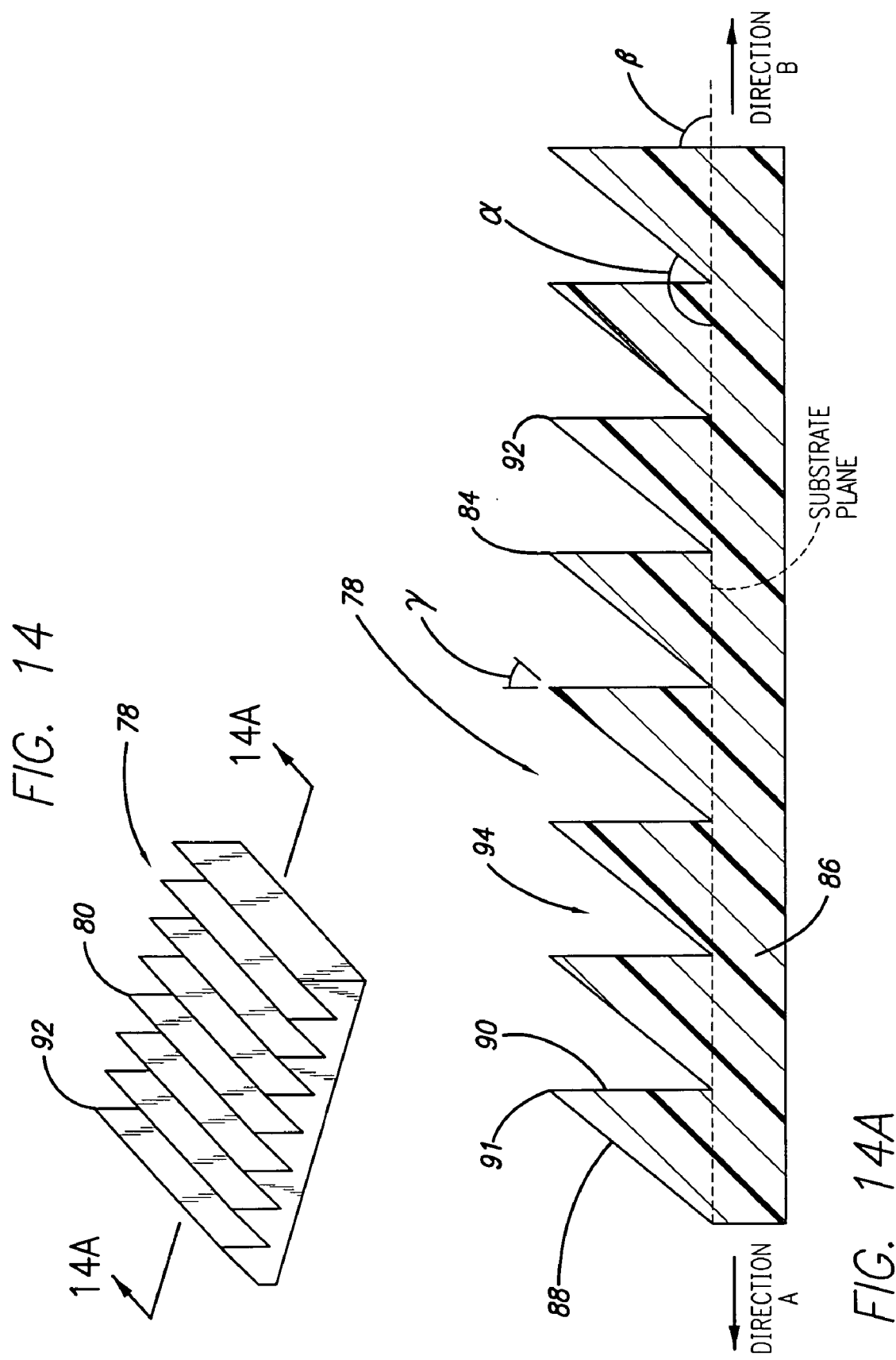
FIG. 14 depicts an enlarged view of another embodiment of a tissue engaging element having surface relief protuberances.

With reference to FIG. 14, a close-up view is provided of another embodiment wherein a tissue engaging element 78 has surface relief protuberances 80 that are manufactured according to a prescribed pattern. As illustrated in FIG. 14A, which is a cross-section of FIG. 14 taken along line 14A-14A, the tissue engaging element has several rows of elongate protuberances 84. The protuberances extend from a substrate 86 of the engaging element. Each protuberance has a first planar surface 88 and a second planar surface 90 that intersect along an edge 91. In the illustrated embodiment, the edge also has a peak 92, which is the furthest point from the substrate of the engaging element. There is a space 94 between adjacent protuberance peaks. When the engaging element is placed in contact with the tissue of the heart, the protuberances produce a friction force which is greatest in a direction generally transverse to the edges of the protuberances. The tissue engaging element is configured so that the protuberances engage the surface tissue of the heart without substantially penetrating the heart surface and so as to create a friction force that will resist migration of the tissue engaging element.

With continued reference to FIGS. 14 and 14A, each of the protuberances 84 may be viewed as defined by an first angle α, a second angle β, and an edge or peak angle γ. The first angle is formed by the intersection of the first planar surface 88 and a plane defined by the extent of the substrate 86. The second angle is formed by the intersection of the second planar surface 90 and the plane of the substrate. The edge angle is defined by the intersection of the first and second surfaces. In the embodiment illustrated in FIGS. 14 and 14A, the first angle is about 135 degrees, the second angle is about 90 degrees and the edge angle is about 45°. It should be understood that, in other embodiments, the first and second angles may be different. It will be appreciated that changing the size, angles and/or the spacing of the protuberances changes the level and behavior of the friction forces between the engaging element and the heart surface, and thus affects the behavior of the tissue engaging element in suppressing migration of the harness on the heart surface.

With continued references to FIGS. 14 and 14A, the first plane angle α is greater than the second plane angle β. In this arrangement, a frictional force resisting migration of the engagement element in direction B is greater than a frictional force resisting migration of the engagement element in direction A. Thus, the engagement element of FIGS. 14 and 14A exhibits preferential migration resistance in direction B.

In accordance with one embodiment, several such preferentially directional engagement elements are installed on a cardiac harness so that the harness preferentially resists migration in a direction that is generally downwardly relative to a longitudinal axis of the heart. As such, the harness will preferentially migrate upwardly toward the base of the heart. Preferably, the structure of the harness at and around the apex is configured to prevent the harness from moving too far upwardly. Simultaneously, the directional engagement elements prevent the harness from working itself downwardly over the apex and off of the heart. Thus, the harness is held snugly in place.

In another embodiment, a plurality of directional engagement elements are disposed in various orientations around the harness. Although each engagement element exhibits preferential migration resistance, the combined effect of the plurality of variously-arranged elements holds the harness in place on the heart without substantial preferential migration in any direction. In still another embodiment, directional engagement elements are disposed on the harness so that certain zones of the harness have a preferential migration resistance. Thus, certain portions of the harness will tend to migrate in a preferred direction. For example, a right side of the harness may be configured to preferentially migrate upwardly so that the harness covers a greater proportion of the right ventricle which, as discussed above, extends farther from the apex than does the left ventricle.

With reference next to FIGS. 15 and 15A, a close-up view is provided of another embodiment wherein a tissue engaging element 78 has surface relief protuberances 80 that are manufactured according to a prescribed pattern. The tissue engaging element shown in FIG. 15 is similar to the tissue engaging element shown in FIG. 14, except as described below. As best illustrated in FIG. 15A, which is a cross-section of FIG. 15, taken along line 15A-15A, on a first side 96 of a dividing line of the tissue engaging element, the protuberances 84 are oriented in a first arrangement that preferentially resists movement in direction A. On a second side 98 of the dividing line of the tissue engaging element, the protuberances are oriented in a second arrangement that preferentially resists movement in direction B. It will be appreciated that because the directions A and B are opposite to one another, the engaging element produces oppositely directed friction forces on the heart surface. Thus, the tissue engaging element resists migration in both directions A and B.

In the embodiment illustrated in FIGS. 15 and 15A, the first angle α is about 90 degrees and the second angle β is about 135 degrees in the first arrangement, but the first angle is about 135° and the second angle is about 90° in the second arrangement. It is to be understood that plane angles need not be uniform throughout an engagement element and, in some embodiments adjacent protuberances may have different plane angles.

FIGS. 16 and 16A illustrate another embodiment of a tissue engaging element 78 which is capable of gripping the surface tissue of the heart. The tissue engaging element illustrated in FIGS. 16-16A, is substantially similar to the engaging element illustrated in FIGS. 15-15A. However, the plane angles α and β in FIGS. 16-16A differ from those of FIGS. 15-15A. For example, on the first side 96, the first angle is acute and the second angle is an obtuse angle of more than about 135°. A similar embodiment of a tissue engaging element 78 is illustrated in FIGS. 17 and 17A. The tissue engaging element illustrated in FIGS. 17-17A has a space 94 between adjacent protuberances 84. It will be appreciated that changing the size, angles and/or the spacing of the protuberances changes the level of the friction force which the engaging element can exert on the heart surface, and thus affects the level to which the tissue engaging element suppresses migration of the harness on the heart surface.

Figure 18:
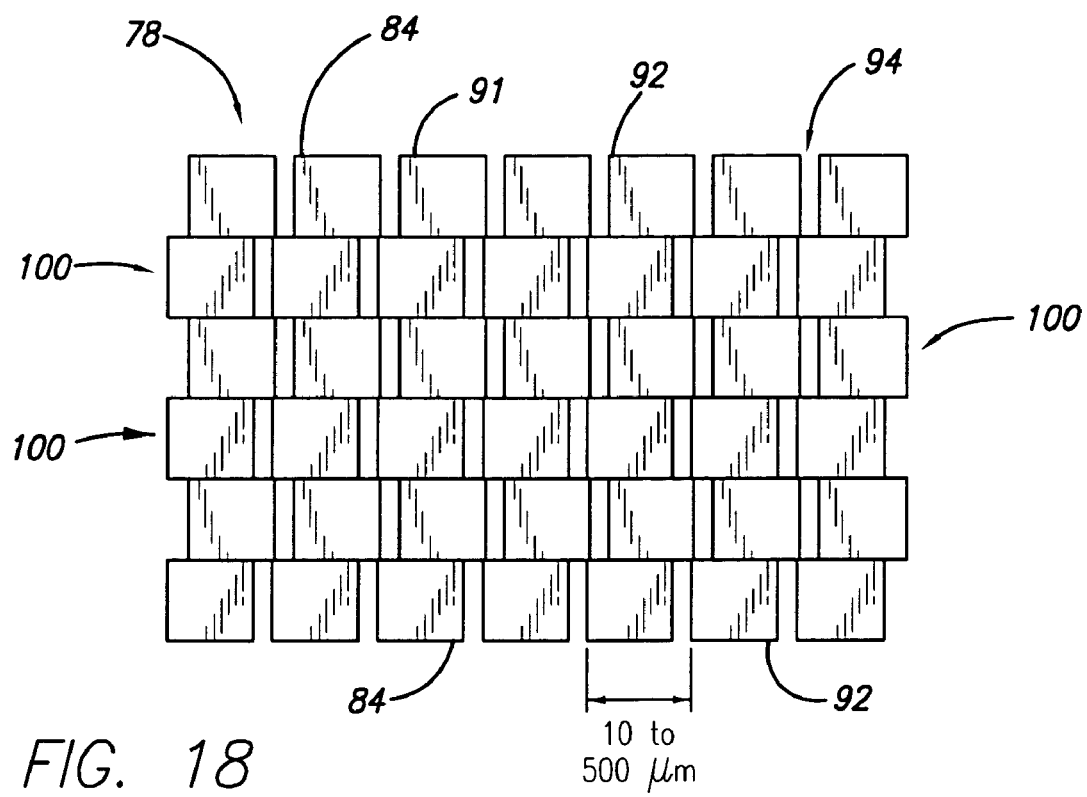
FIG. 18 depicts a plan view of one embodiment of a tissue engaging element having a surface formed by several rows of protuberances that do not extend all the way across the engagement element.
Figure 18A:
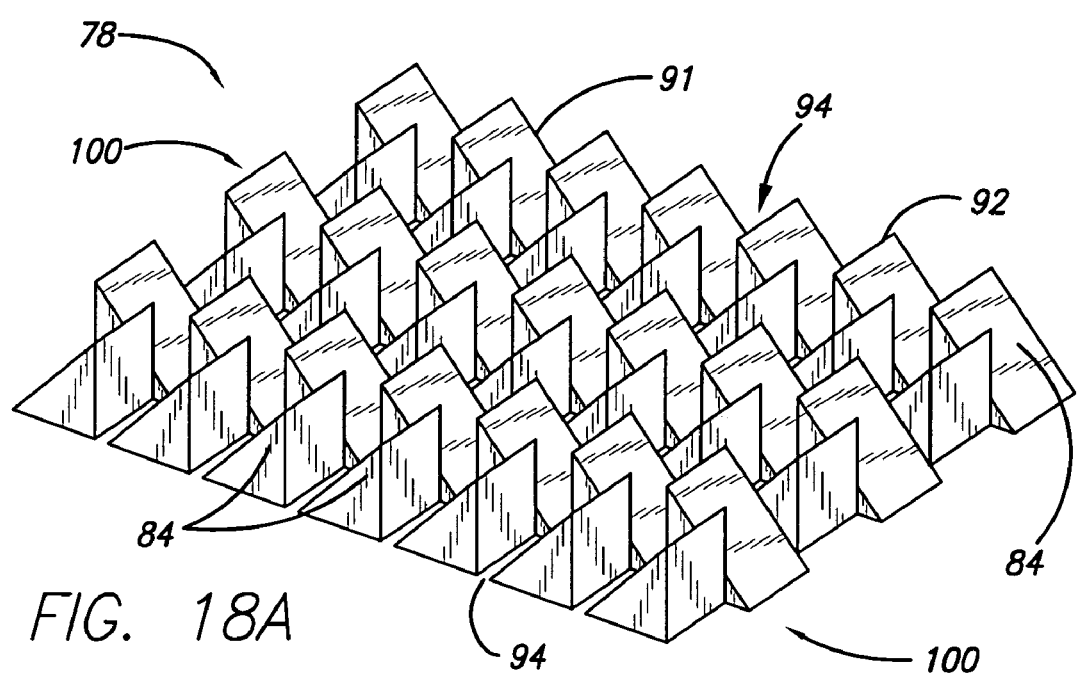
FIG. 18A depicts a perspective view of the tissue engaging element of FIG. 18.
Figure 19:
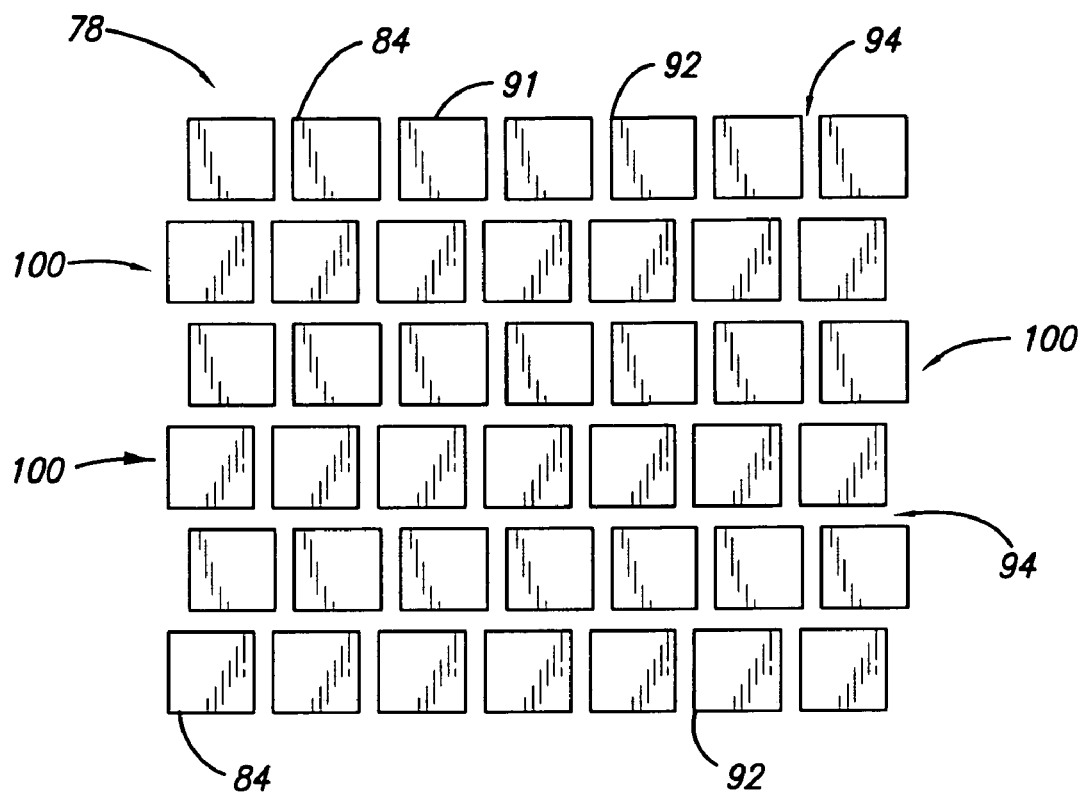
FIG. 19 depicts a plan view of another embodiment of a tissue engaging element having a surface formed by several rows of protuberances that are spaced apart from adjacent rows of protuberances.
Figure 19A:
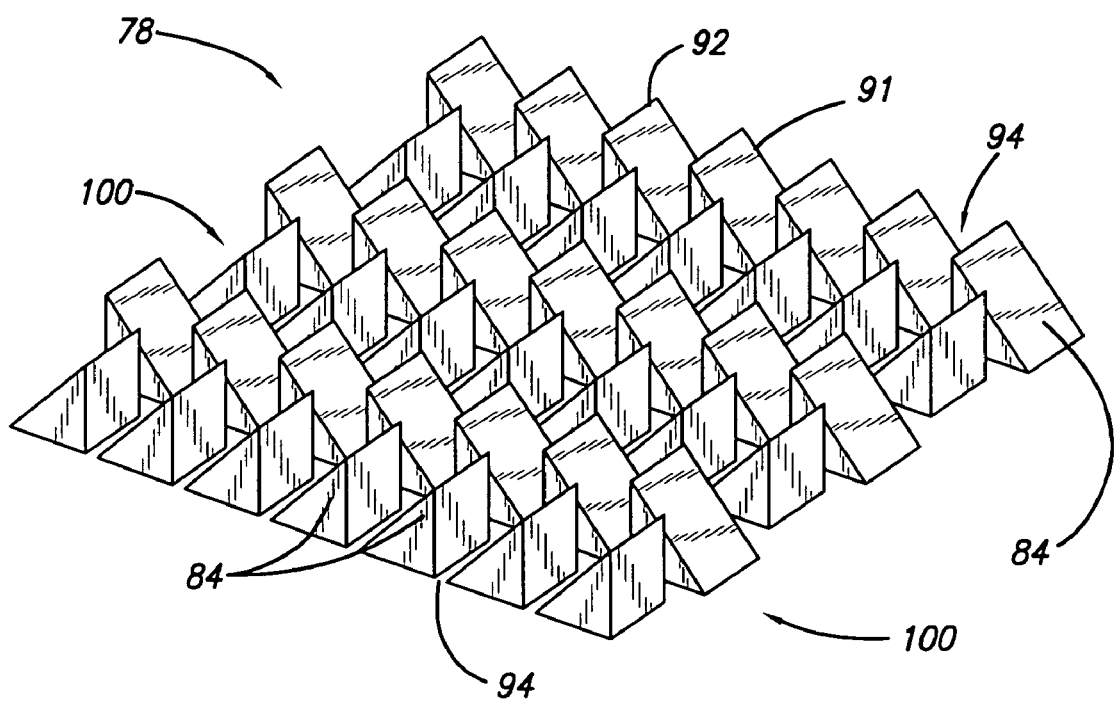
FIG. 19A depicts a perspective view of the tissue engaging element of FIG. 19.

FIGS. 18 and 18A illustrate one embodiment of a tissue engaging element 78 which has a surface relief formed by several rows of protuberances 84. The protuberances illustrated in FIGS. 18-18A are substantially similar to the elongate protuberances illustrated in FIGS. 14-14A. However, the protuberances illustrated in FIGS. 18-18A do not extend all the way across the engagement element. Instead, a plurality of rows 100 of protuberances are disposed adjacent one another. As best shown in FIG. 18A, each protuberance terminates with an upper-most edge which also has a peak 92. As there are several protuberances in each row, there is a space 94 between adjacent protuberance peaks. The protuberances in each row preferably have a peak-to-peak spacing of about 10 µm to 500 µm. Each row is arranged to preferentially frictionally resist movement in one direction. Adjacent rows preferably have opposite preferred resistance directions. In other embodiments, the adjacent rows may be spaced apart from one another. For example, in the embodiment illustrated in FIGS. 19 and 19A, adjacent rows are separated by a space 94. With reference to FIGS. 18 through 19A, it will be appreciated that because adjacent rows are capable of producing friction forces in opposite directions on the heart surface, the totality of the rows forming the tissue engaging element are capable of producing friction forces which grip the surface tissue of the heart.

Figure 20:
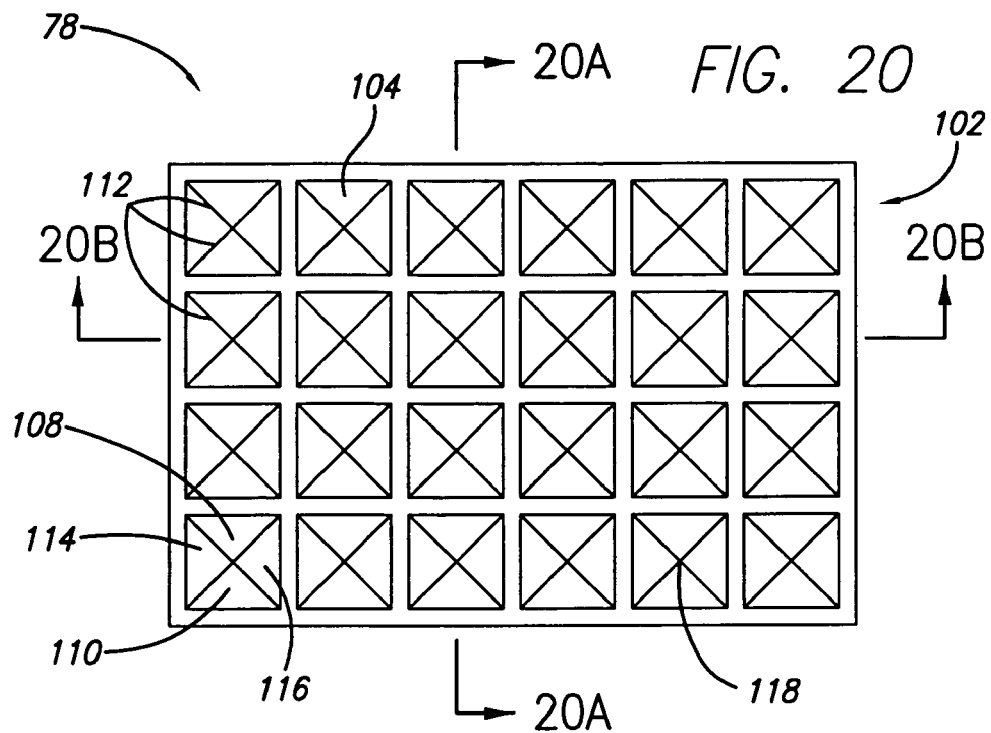
FIG. 20 depicts a plan view of an embodiment of a tissue engaging element having pyramid-shaped surface relief protuberances arranged into a row/column structure.
Figure 20A:
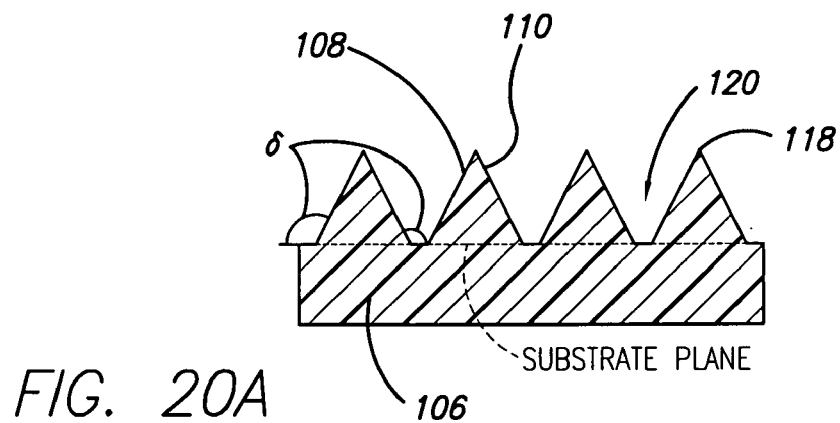
FIG. 20A depicts a partial cross-section of the tissue engaging element taken along ling 20A-20A of FIG. 20.
Figure 20B:
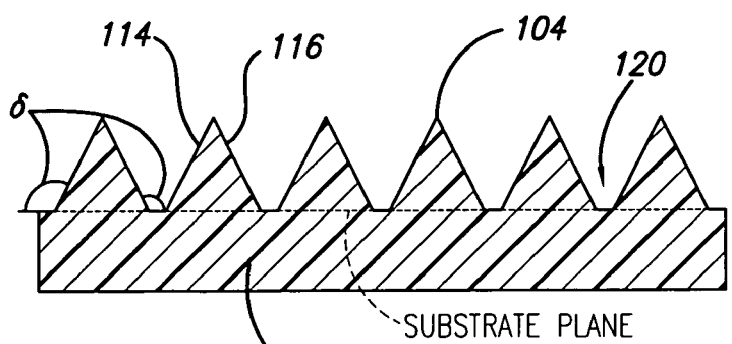
FIG. 20B depicts a partial cross-section of the tissue engaging element taken along ling 20B-20B of FIG. 20.

With reference next to FIG. 20, one embodiment of a tissue engaging element 78 has surface relief protuberances 102 that are arranged into a row/column structure. As shown in FIG. 20A, which is a cross-section of FIG. 20 taken along line 20A-20A, the tissue engaging element has a surface relief formed by several rows of protuberances 104. The protuberances extend from a substrate 106 of the engaging element. Each protuberance has a first planar surface 108 and a second planar surface 110 that intersect along an edge 112. Similarly, as shown in FIG. 20B, which is a cross-section of FIG. 20 taken along line 20B-20B, the surface relief protuberances of the engaging element are divided into several columns. Each protuberance comprises a third planar surface 114 and a fourth planar surface 116 that intersect along an edge. As illustrated in FIG. 20 the edges formed by the planar surfaces intersect at a peak 118, which is the furthest point from the substrate of the engaging element. In the illustrated embodiment, the peak is generally pointed, and the edges at which the planes intersect are not elongate.

With continued reference to FIG. 20, each of the planar surfaces 108, 110, 114 and 116 has an inclination angle δ. The inclination angle is formed by the intersection of the planar surface and a plane defined by the surface of the substrate. In the illustrated embodiment, the four planar surfaces have equal inclination angles, thus giving the protuberances a pyramid shape. As there are several rows and columns of protuberances, there is a space 120 between adjacent protuberance peaks. When the tissue engaging element is placed in contact with the heart surface, the protuberances engage the surface tissue without substantially penetrating the heart surface so as to create a friction force that will resist migration of the tissue engaging element relative to the heart surface.

Figure 21:
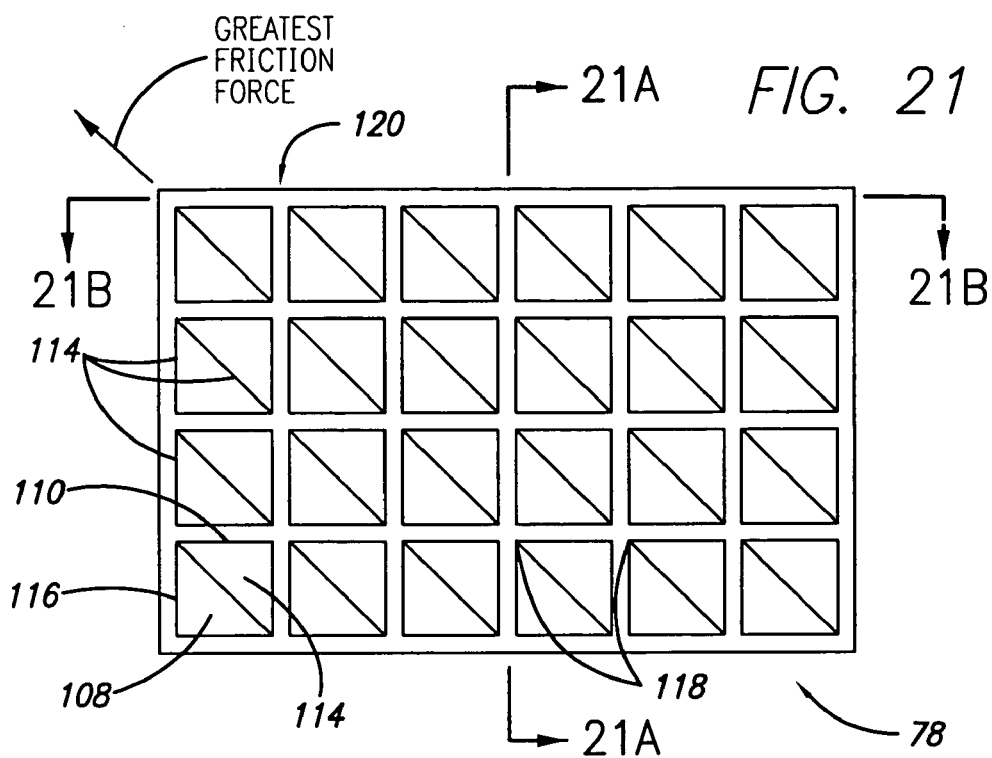
FIG. 21 depicts a plan view of an embodiment of a tissue engaging element having surface relief protuberances arranged into a row/column structure.

With continued reference to FIG. 20, because the planar surfaces 108, 110, 114 and 116 have the same inclination angles δ, the peaks 118 are centrally positioned within the pyramid-shaped protuberances. Thus, the tissue engaging element produces friction forces that resist migration of the harness generally equally in directions facing each plane. In another embodiment, the peaks are advantageously positioned off-center so that frictional forces resisting migration in a first direction are greater than frictional forces resisting migration is a second direction. FIG. 21 illustrates one embodiment of a tissue engaging element that has pyramid-shaped protuberances with off-center peaks.

Figure 21A:
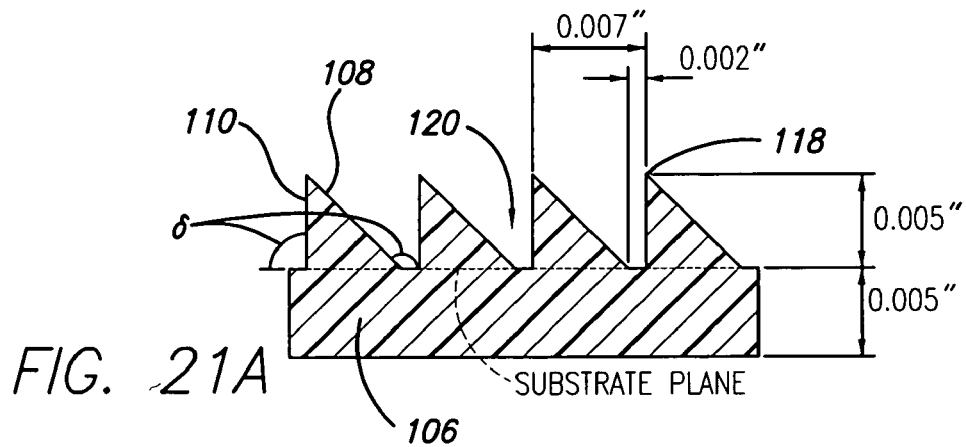
FIG. 21A depicts a partial cross-section of the tissue engaging element taken along ling 21A-21A of FIG. 21.
Figure 21B:
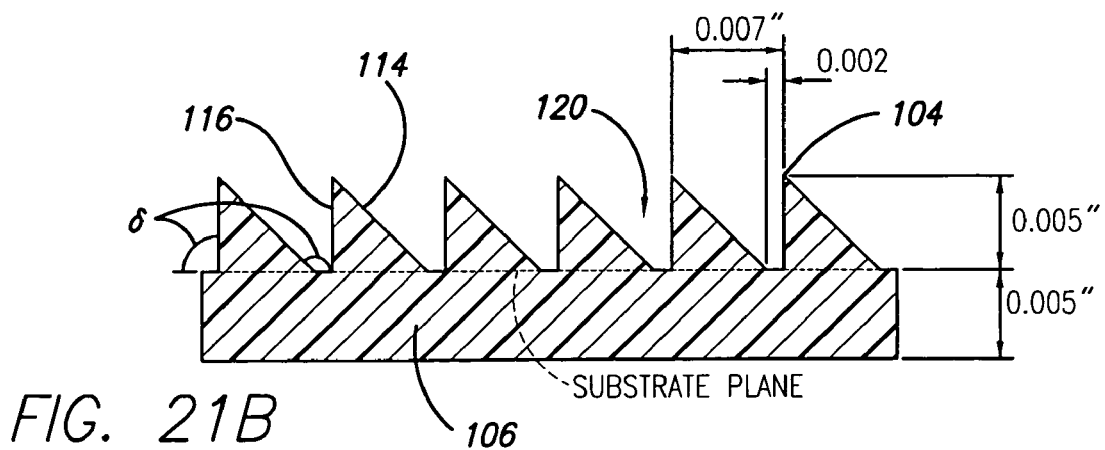
FIG. 21B depicts a partial cross-section of the tissue engaging element taken along ling 21B-21B of FIG. 21.

As shown in FIG. 21A, which is a cross-section of FIG. 21 taken along line 21A-21A, the tissue engaging element 78 has a surface relief formed by several rows and columns of protuberances 104. The protuberances extend from a substrate 106 of the engaging element. Each protuberance has a first planar surface 108 and a second planar surface 110 that intersect along an edge 112. Similarly, as shown in FIG. 21B, which is a cross section of FIG. 21 taken along line 21B-21B, the surface relief protuberances are arranged into several columns that extend from the substrate of the engaging element. Each protuberance has a third planar surface 114 and a fourth planar surface 116 that intersect along an edge 117. As illustrated in FIG. 21 the edges formed by the planar surfaces intersect at a peak 118, which is the furthest point from the substrate of the engaging element. In one embodiment, the protuberances extend to a height of about 0.005 inches or less above the substrate. The peaks are separated from adjacent peaks within the same row/column by a distance of about 0.007 inches.

With continued reference to FIG. 21, each of the planar surfaces 108, 110, 114 and 116 of the protuberances 104 can be viewed as defined by an inclination angle δ. The inclination angle is formed by the intersection of the planar surface and a plane defined by the surface of the substrate 106. In the illustrated embodiment, the inclination and third planar surfaces have equal inclination angles of about 135 degrees, while the second and fourth planar surfaces have equal inclination angles of about 90 degrees. Because of the difference in inclination angles, the peaks 118 are not centrally positioned on the protuberances. Instead, the peaks are off center as shown in FIG. 21. When the tissue engaging element is placed in contact with the tissue of the heart, the off-center peaks of the protuberances engage the surface tissue of the heart so as to create friction forces that provide greater resistance to migration of the tissue engaging element in a first direction than in a second direction.

It is to be noted that in other embodiments, the inclination angles of the second and fourth planar surfaces may be greater than or lesser than about 90 degrees. Likewise, in other embodiments the inclination angles of the first and third planar surfaces may be greater than or lesser than about 135 degrees. In still other embodiments, the inclination angles of all the planar surfaces may advantageously be varied from the angles illustrated herein. It is to be further noted that although FIGS. 20 and 21 show protuberances having four planar surfaces, in other embodiments the protuberances can be comprised of more than or lesser than four planar surfaces.

Figure 22:
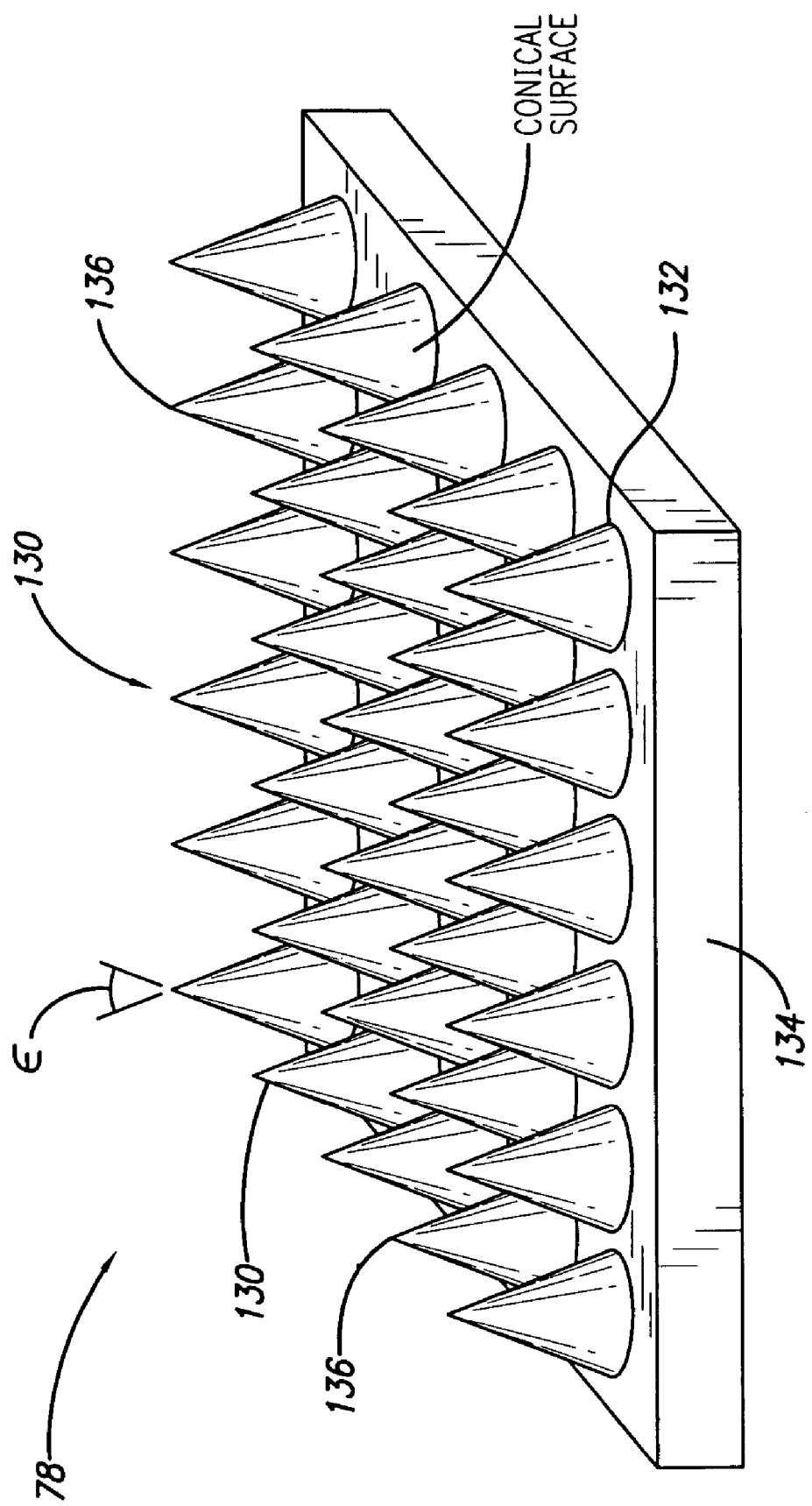
FIG. 22 depicts a perspective view of another embodiment of a tissue engaging element having surface relief protuberances with conical-shaped surfaces.

With reference next to FIG. 22, another embodiment of a tissue engaging element 78 is illustrated. The tissue engaging element shown in FIG. 22 has several rows of protuberances 130 having conical surfaces. The conical surface of each protuberance extends from a base 132 at a substrate 134 and terminates in a generally pointed peak 136. The several protuberances comprising the engaging element are arranged into a row/column structure. Of course, it is to be understood that other embodiments may not employ such a row/column structure.

With continued reference to FIG. 22, the peaks 136 of the conical protuberances 130 are centrally positioned. In one embodiment, each of the peaks has an angle ε of about 60 degrees. In other embodiments, however, the angle of the peaks may be greater than or lesser than about 60 degrees. For example, the peak angle preferably is less than about 135°. More preferably the peak angle is between about 15-115°, and more preferably is between about 30-90°. Most preferably the peak angle is between about 45-75°. In any case, the peak angle and peak height preferably are arranged so that the protuberances will not substantially penetrate the heart surface when the element is engaged with heart tissue.

FIGS. 23A and 23B illustrate one embodiment of a tissue engaging element 78 having conical protuberances 130. In the embodiment shown in FIGS. 23A and 23B, the bases 132 of adjacent protuberances are spaced from one another.

In other embodiments, the peaks 136 of the conical protuberances 130 may be positioned off center. Thus, when the tissue engaging element is placed in contact with the tissue of the heart, the off-center peaks of the protuberances create preferential friction forces that preferentially resist migration of the tissue engaging element in at least one direction.

The tissue engaging elements disclosed herein can be manufactured by any of many processes and of many appropriate materials. Preferably, the material to be formed into the protuberances is less compliant than the heart wall so that the protuberances can effectively engage the heart wall. The protuberances preferably extend from the substrate a distance comparable to the size of the grit discussed in previous embodiments. Preferably, the protuberances extend between about 10 to 500 micrometers from the substrate. In other embodiments, the protuberances are between about 50 to 250 micrometers high, or are between about 60 to 200 micrometers. In a still further embodiment, the protuberances are between about 50 to 125 micrometers high. In yet another embodiment, the protuberances are between about 200 to 400 micrometers high.

Moreover, although the protuberances engage the heart surface, they preferably are configured so that they do not substantially penetrate the heart surface due to the size of the protuberances and the characteristics of the peak. This should be taken to mean that the protuberances engaging the heart surface do not penetrate the heart epicardium sufficient to cause debilitating injury to the heart. Further, the protuberances do not penetrate the tissue enough to puncture any coronary vessel wall.

With reference to FIGS. 24 and 24A, one example of a method and apparatus for making an engagement element 78 is provided. FIGS. 24 and 24A disclose a mold 138 for forming an array of conical protuberances 130 as shown and discussed in connection with the embodiment shown in FIGS. 23A-23B. As shown in FIGS. 24 and 24A, the mold includes a base portion 140 and a protuberances portion 142. The protuberances preferably are spaced between 5-500 micrometers apart. In the illustrated embodiment, the mold is capable of making a tissue engaging element which is about 0.175 inch long by about 0.075 inch wide.

In operation, the mold 138 preferably is filled with a resin such as cyanoacrylate, and a vacuum is drawn in order to draw the cyanoacrylate into the protuberance molds. Upon drying, the engaging element can be applied to a harness. The engaging element may be adhered directly to the harness or sutured or otherwise applied. In the embodiment illustrated in FIG. 3, adjacent elastic members are connected by silicone rubber connectors, and tissue engaging elements are adhered to the silicone rubber connectors. In other embodiments, the connectors of the harness are unitarily formed to include protuberances similar to an engaging element. In still other embodiments, a harness can be formed having tissue engaging elements co-formed therewith.

Several other types of materials and prostheses can be used to construct tissue engaging elements. For example, a block of material can be machined to create the element. In other embodiments, relatively large extrusions of material can be cut into several smaller tissue engaging elements. In another preferred embodiment, tissue engaging elements are formed by injection molding. Preferably, the tissue engaging elements are formed of an injection molded polymer, such as urethane. In still another embodiment, tissue engaging elements are constructed of a metal material. During manufacture, the metal is etched electrochemically or otherwise to form surface relief protuberances.

In embodiments discussed above, surface relief protuberances have been depicted as having generally planar surfaces. It is to be understood that, in other embodiments, protuberances having curved, undulating, or even roughened surfaces can be employed.

In the embodiments discussed and illustrated above, aspects of the present invention have been discussed in connection with a cardiac harness embodiment employing elastic rows. In such an embodiment, the harness has an at-rest size that is smaller than the heart, and is elastically deformed to fit the device over the heart. As such, the harness engages the surface of the heart throughout the heart cycle. Also, the harness exerts an inwardly-directed force throughout the heart cycle. This force aids heart function and also forcibly engages the tissue engaging elements with the heart surface. It is to be understood that the aspects discussed above can also be practiced with a cardiac harness having different properties than the illustrated harness. For example, a partially elastic or substantially non-elastic cardiac harness can also benefit from aspects of the embodiments discussed above. In such harnesses, the tissue engaging elements may not be forcibly engaged with the heart surface throughout the entire cardiac cycle. However, the elements will be engaged with the heart surface during at least part of the cycle due to the expansion of the heart and engagement with the harness.

Although the present invention has been described in terms of certain preferred embodiments, other embodiments that are apparent to those of ordinary skill in the art are also within the scope of the invention. Accordingly, the scope of the invention is intended to be defined only by reference to the appended claims. While the dimensions, types of materials and types of engaging elements described herein are intended to define the parameters of the invention, they are by no means limiting and are exemplary embodiments.

We claim:

1. A self-anchoring cardiac harness, comprising:
   a plurality of circumferential rings of elastic undulating elements, the majority of the rings being sized to circumferentially surround an outer surface of the heart in conformity with the general anatomy of a portion of the patient's heart; and
   a plurality of connecting members having a friction enhancing surface adapted for restricting migration of the harness in relation to the outer surface of the heart without substantially penetrating the heart wall, wherein a portion of the adjacent rings extend through the connecting members.

2. The self-anchoring cardiac harness of claim 1, wherein the friction enhancing surface includes a grit.

3. The self-anchoring cardiac harness of claim 1, wherein the friction enhancing surface includes a suction cup.

4. The self-anchoring cardiac harness of claim 1, wherein the friction enhancing surface includes a plurality of protuberances, the protuberances having a configuration including at least two planar sides extending from a substrate.

5. The self-anchoring cardiac harness of claim 4, wherein the protuberances are spaced apart on the connecting member.

6. The self-anchoring cardiac harness of claim 4, wherein the protuberances cover the entire substrate.

7. The self-anchoring cardiac harness of claim 1, wherein the friction enhancing surface includes a plurality of protuberances, the protuberances having a pyramidal configuration.

8. The self-anchoring cardiac harness of claim 1, wherein the protuberances are conical.

9. The self-anchoring cardiac harness of claim 1, wherein the friction enhancing surface is formed from a semi-compliant material.

10. The self-anchoring cardiac harness of claim 9, wherein the semi-compliant material is silicone.

11. The self-anchoring cardiac harness of claim 9, wherein the semi-compliant material is a polymer.

12. The self-anchoring cardiac harness of claim 1, wherein the friction enhancing surface includes a plurality of protuberances disposed on a substrate, and the protuberances extend between about 10-500 μm above the substrate.

13. The self-anchoring cardiac harness of claim 1, wherein the friction enhancing surface is configured to not penetrate the epicardium.

14. The self-anchoring cardiac harness of claim 1, wherein the friction enhancing surface is molded into the connecting members.

15. A self-anchoring cardiac harness, comprising:
 a plurality of rows formed from elastic undulating elements, the majority of the rows being joined at their opposite ends to form rings of various sized circumferences such that each ring is adapted to circumferentially surround an outer surface of the heart in conformity with the general anatomy of a portion of the patient's heart;
 a plurality of connecting members linking adjacent circumferential rings; and
 a plurality of tubular friction enhancing members disposed on the harness and adapted for restricting migration of the harness in relation to the outer surface of the heart, the tubular friction enhancing members having a lumen which receives at least one elastic undulating element therein.

16. The self-anchoring cardiac harness of claim 15, wherein the tubular friction enhancing members are formed from a semi-compliant material.

17. The self-anchoring cardiac harness of claim 15, wherein the tubular friction enhancing members are configured with an irregular non-piercing surface.

18. The self-anchoring cardiac harness of claim 17, wherein the non-piercing surface is molded into the surface of the tubular friction enhancing surface.

19. The self-anchoring cardiac harness of claim 15, wherein the opposite ends of the rings are joined by connective junctions.

20. The self-anchoring cardiac harness of claim 15, wherein the cardiac harness is configured to be delivered minimally invasively.

21. The self-anchoring cardiac harness of claim 15, wherein the tubular friction enhancing members includes a plurality of protuberances, the protuberances having a configuration including at least two planar sides extending from a substrate.

22. The self-anchoring cardiac harness of claim 21, wherein the protuberances are spaced apart on the connecting member.

23. The self-anchoring cardiac harness of claim 21, wherein the protuberances cover the entire substrate.

24. The self-anchoring cardiac harness of claim 15, wherein the tubular friction enhancing members include a grit.

25. The self-anchoring cardiac harness of claim 15, wherein the tubular friction enhancing members include a suction cup.

26. The self-anchoring cardiac harness of claim 15, wherein the tubular friction enhancing members are configured to not substantially penetrate the heart wall.

* * * * *

UNITED STATES PATENT AND TRADEMARK OFFICE
CERTIFICATE OF CORRECTION

| | | |
|---|---|---|
| PATENT NO. | : 7,291,105 B2 | Page 1 of 1 |
| APPLICATION NO. | : 10/888806 | |
| DATED | : November 6, 2007 | |
| INVENTOR(S) | : Lilip Lau et al. | |

It is certified that error appears in the above-identified patent and that said Letters Patent is hereby corrected as shown below:

Title Page; item (56);

References Cited, Page 3, insert --6,517,570 B1 2/2003 Lau et al.--

References Cited, Page 3, delete "WO 00/43919" and insert --WO 00/42919--

References Cited, Page 3, insert --WO WO 00/36995 6/2000--

Signed and Sealed this

First Day of July, 2008

JON W. DUDAS
*Director of the United States Patent and Trademark Office*